United States Patent [19]
Pratt et al.

[11] Patent Number: 5,792,150
[45] Date of Patent: Aug. 11, 1998

[54] APPARATUS FOR APPLYING SURGICAL CLIPS WITH IMPROVED JAW AND CLOSURE MECHANISMS

[75] Inventors: James R. Pratt, Solms-Oberbiel, Germany; Gary S. Kappel, Acton, Mass.; Douglas J. Cuny, Bethel, Conn.; H. Jonathan Tovey, Milford, Conn.; Paul J. Phillips, Middlebury, Conn.; Mark S. Peyser, Monroe, Conn.; Ernie Aranyi, Easton, Conn.

[73] Assignee: United States Surgical Corporation, Norwalk, Conn.

[21] Appl. No.: 476,607

[22] Filed: Jun. 7, 1995

Related U.S. Application Data

[63] Continuation-in-part of Ser. No. 134,347, Oct. 8, 1993, Pat. No. 5,607,436.

[51] Int. Cl.⁶ ............................................. A61B 17/00
[52] U.S. Cl. ..................... 606/143; 606/139; 606/157; 227/901
[58] Field of Search .......................... 606/143, 142, 606/139, 151, 205–208

[56] References Cited

U.S. PATENT DOCUMENTS

| | | |
|---|---|---|
| 2,968,041 | 1/1961 | Skold . |
| 3,777,538 | 12/1973 | Weatherly et al. . |
| 3,780,416 | 12/1973 | Rider . |
| 3,955,581 | 5/1976 | Spasiano et al. . |
| 4,027,510 | 6/1977 | Hiltebrandt . |
| 4,152,920 | 5/1979 | Green . |
| 4,166,466 | 9/1979 | Jarvik . |
| 4,185,762 | 1/1980 | Froehlich . |
| 4,188,953 | 2/1980 | Klieman et al. . |
| 4,196,836 | 4/1980 | Becht . |
| 4,226,242 | 10/1980 | Jarvik . |
| 4,228,895 | 10/1980 | Larkin . |
| 4,242,902 | 1/1981 | Green . |
| 4,246,903 | 1/1981 | Larkin . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,372,316 | 2/1983 | Blake, III et al. . |
| 4,394,864 | 7/1983 | Sandhaus . |
| 4,412,539 | 11/1983 | Jarvik . |
| 4,425,915 | 1/1984 | Ivanov . |

(List continued on next page.)

FOREIGN PATENT DOCUMENTS

| | | |
|---|---|---|
| 0068046 | 1/1983 | European Pat. Off. . |
| 0112980 | 7/1984 | European Pat. Off. . |
| 0406724 | 1/1991 | European Pat. Off. . |
| 0409569 | 1/1991 | European Pat. Off. . |
| 2679763 | 2/1993 | France . |
| 2546696 | 4/1976 | Germany . |
| 8202825 | 9/1982 | WIPO . |
| 8910094 | 11/1989 | WIPO . |

OTHER PUBLICATIONS

Information Booklet for "Auto Suture® Premium Surgiclip™ Titanium Disposable Automatic Clip Appliers", ©1988, 1989.

"Ligaclip For Security in Ligation", Ethicon, 1982.

"Deep Surgery Advantage Dramatic New Access Plus Automatic–Feed in Vessel Ligation", Weck, Surgery, Gynecology & Obstetrics, Sep. 1986.

"New Surgical Procedures For Indirect Hernias", Innovative Surgical Devices, Inc., 1989.

*Primary Examiner*—Jeffrey A. Schmidt

[57] ABSTRACT

An apparatus is provided for applying surgical clips which includes provisions for applying a partially closed clip to ducts or shunts during a surgical procedure. The apparatus includes a ratchet mechanism for permitting incremental closure of a pair of jaw members. A slide member is associated with the ratchet mechanism to prevent a movable handle from opening during a closing stroke until the closing stroke is completed.

4 Claims, 25 Drawing Sheets

U.S. PATENT DOCUMENTS

| | | |
|---|---|---|
| 4,430,997 | 2/1984 | DiGiovanni et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,480,641 | 11/1984 | Failla et al. . |
| 4,492,232 | 1/1985 | Green . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,556,058 | 12/1985 | Green . |
| 4,557,263 | 12/1985 | Green . |
| 4,572,183 | 2/1986 | Juska . |
| 4,576,166 | 3/1986 | Montgomery et al. . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,646,740 | 3/1987 | Peters et al. . |
| 4,662,373 | 5/1987 | Montgomery et al. . |
| 4,674,504 | 6/1987 | Klieman et al. . |
| 4,712,549 | 12/1987 | Peters et al. . |
| 4,850,355 | 7/1989 | Brooks et al. . |
| 4,944,443 | 7/1990 | Oddsen et al. . |
| 4,967,949 | 11/1990 | Sandhaus . |
| 5,030,226 | 7/1991 | Green et al. . |
| 5,047,038 | 9/1991 | Peters et al. . |
| 5,049,152 | 9/1991 | Simon et al. . |
| 5,067,958 | 11/1991 | Sandhaus . |
| 5,084,057 | 1/1992 | Green et al. . |
| 5,100,418 | 3/1992 | Yoon et al. . |
| 5,100,420 | 3/1992 | Green et al. . |
| 5,104,394 | 4/1992 | Knoepfler . |
| 5,104,395 | 4/1992 | Thornton et al. . |
| 5,112,343 | 5/1992 | Thornton . |
| 5,163,945 | 11/1992 | Ortiz et al. . |
| 5,171,247 | 12/1992 | Hughett et al. . |
| 5,171,249 | 12/1992 | Stefanchik et al. . |
| 5,192,288 | 3/1993 | Thompson et al. . |
| 5,199,566 | 4/1993 | Ortiz et al. . |
| 5,207,691 | 5/1993 | Nardella . |
| 5,246,156 | 9/1993 | Rothfuss et al. . |
| 5,246,450 | 9/1993 | Thornton et al. . |
| 5,282,807 | 2/1994 | Knoepfler . |
| 5,282,808 | 2/1994 | Kovac et al. . |
| 5,290,299 | 3/1994 | Fain et al. . |
| 5,306,280 | 4/1994 | Bregen et al. . |
| 5,333,772 | 8/1994 | Rothfuss et al. . |
| 5,447,513 | 9/1995 | Davison et al. .................. 606/143 |

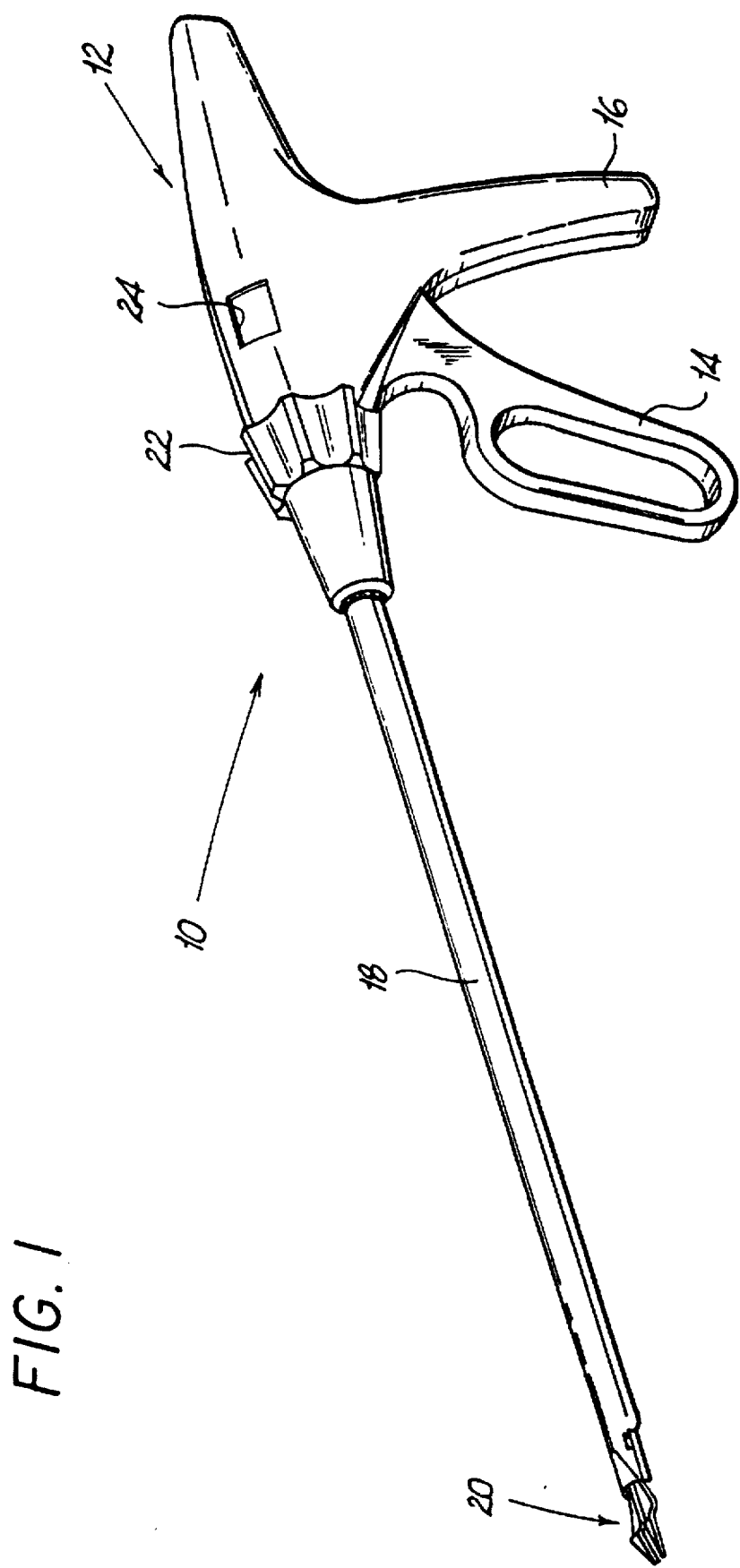

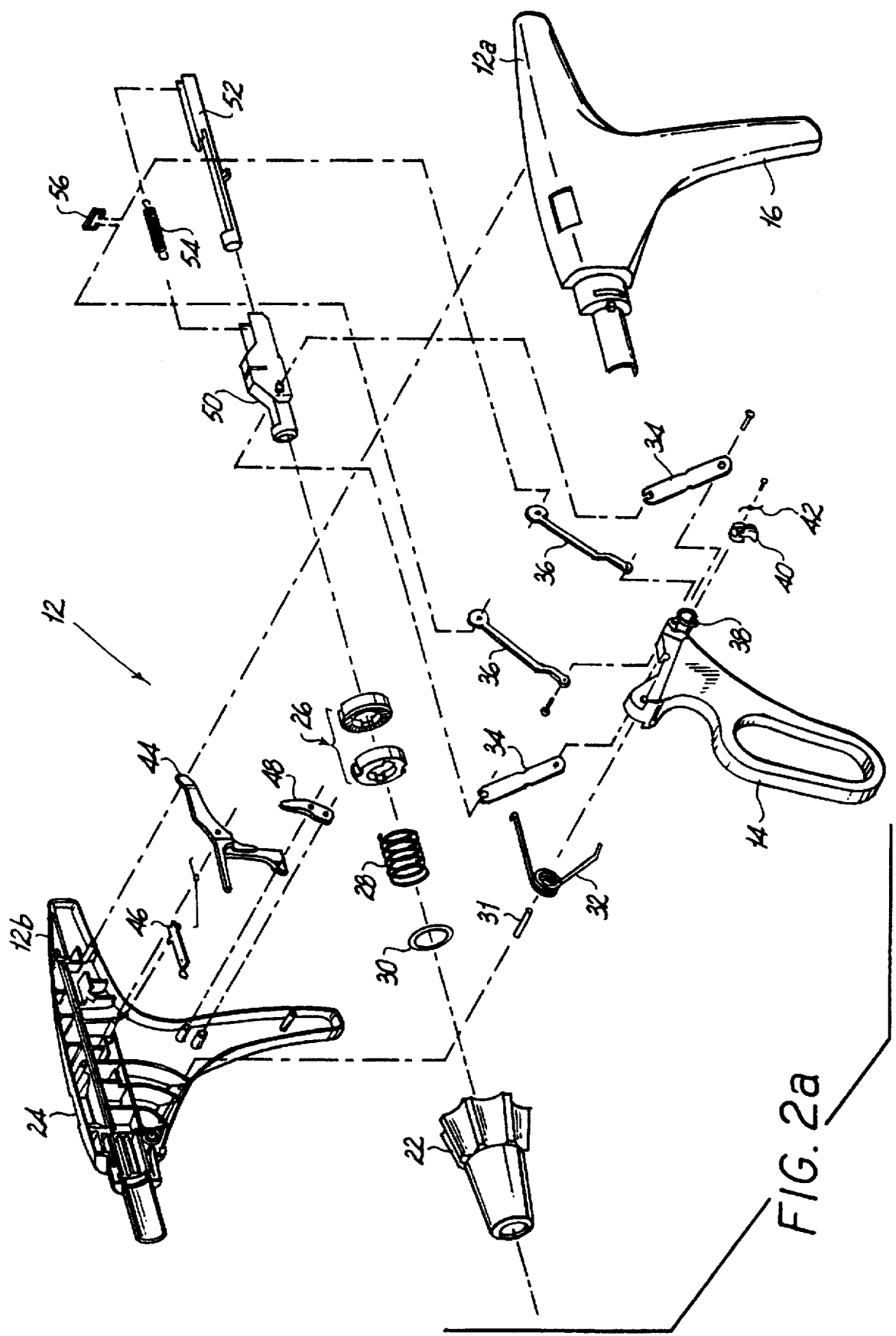

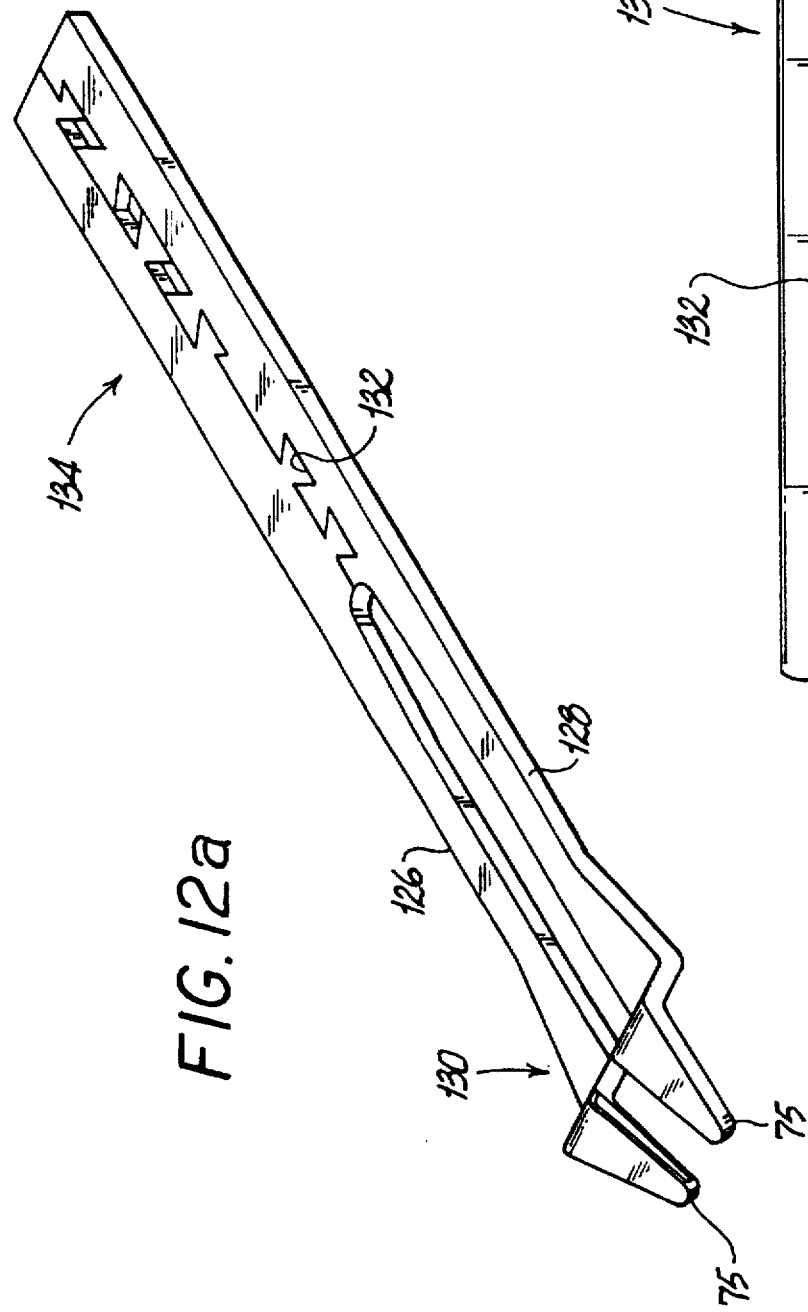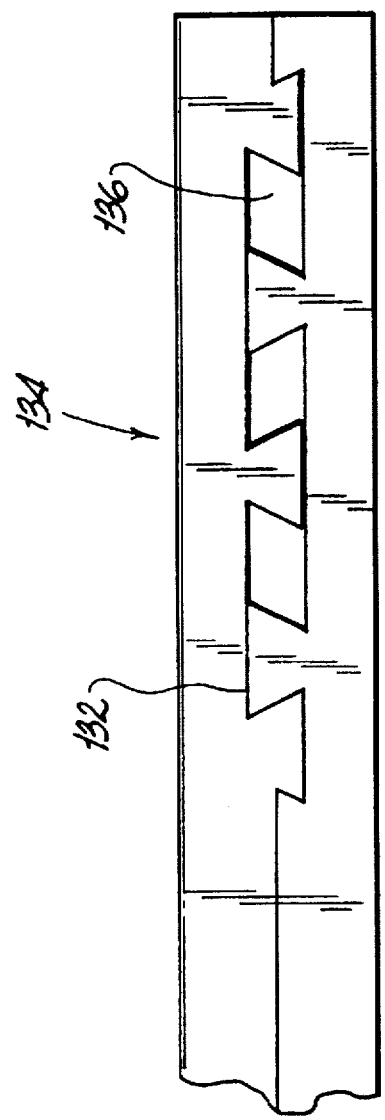

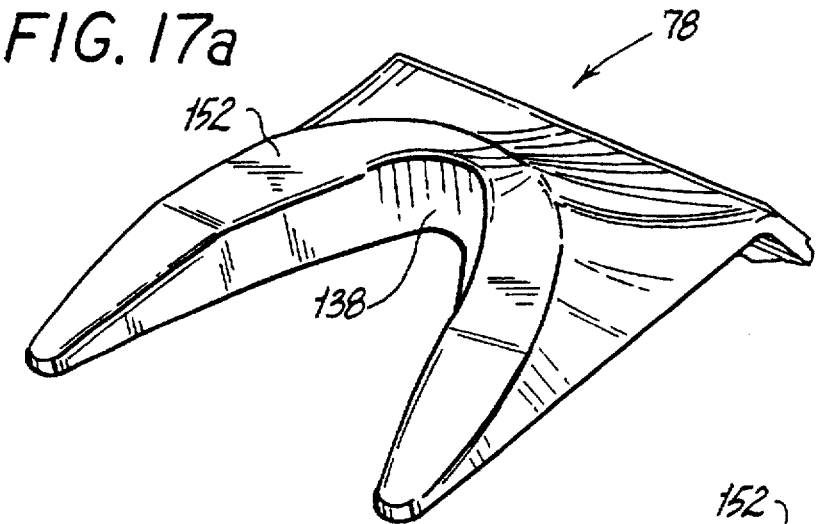
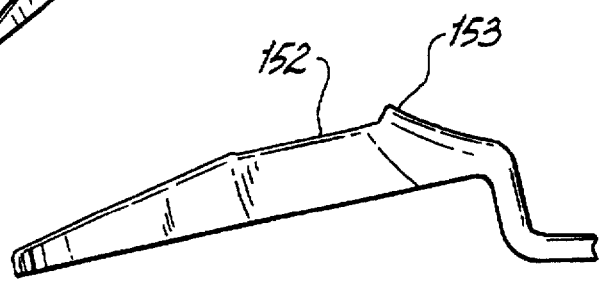
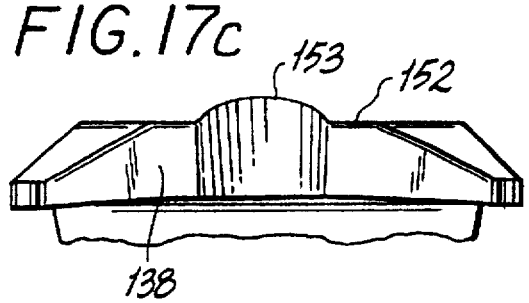
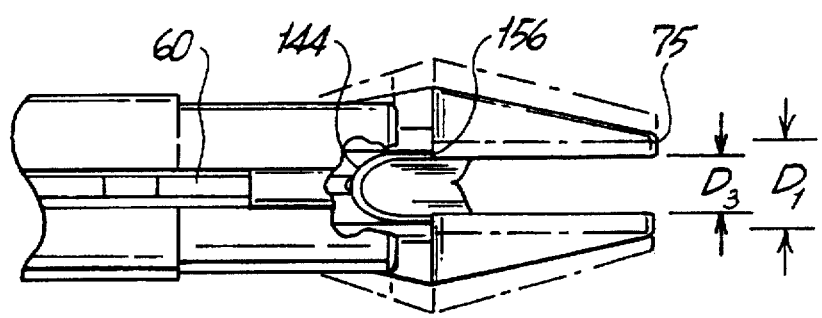
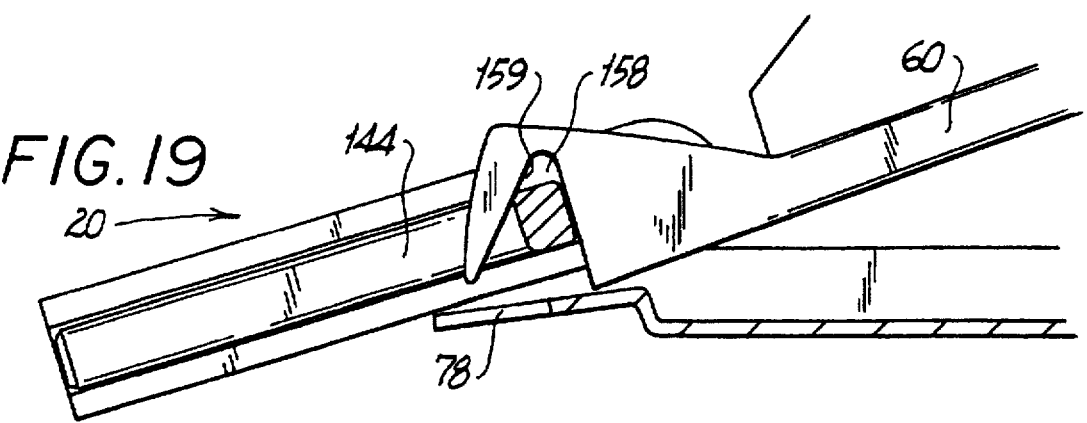

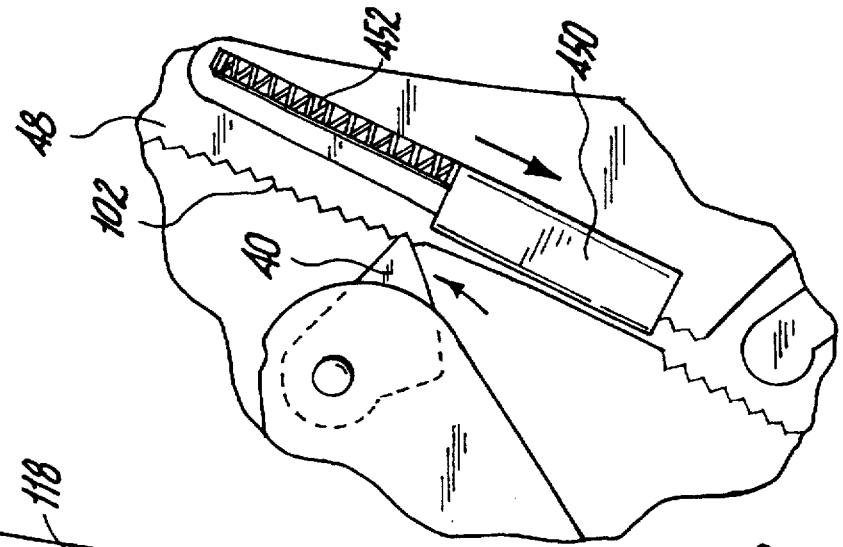
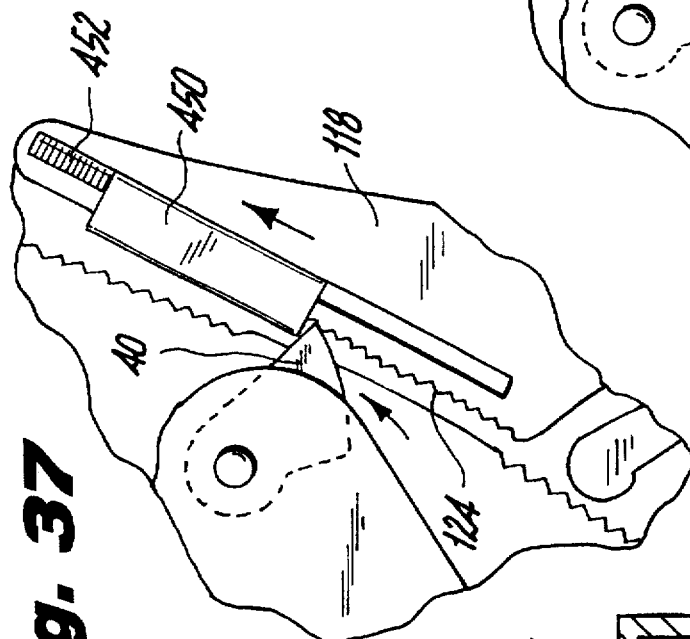
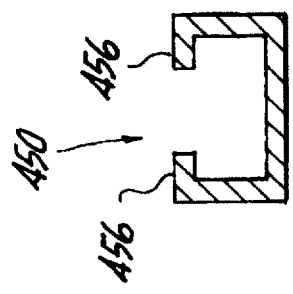
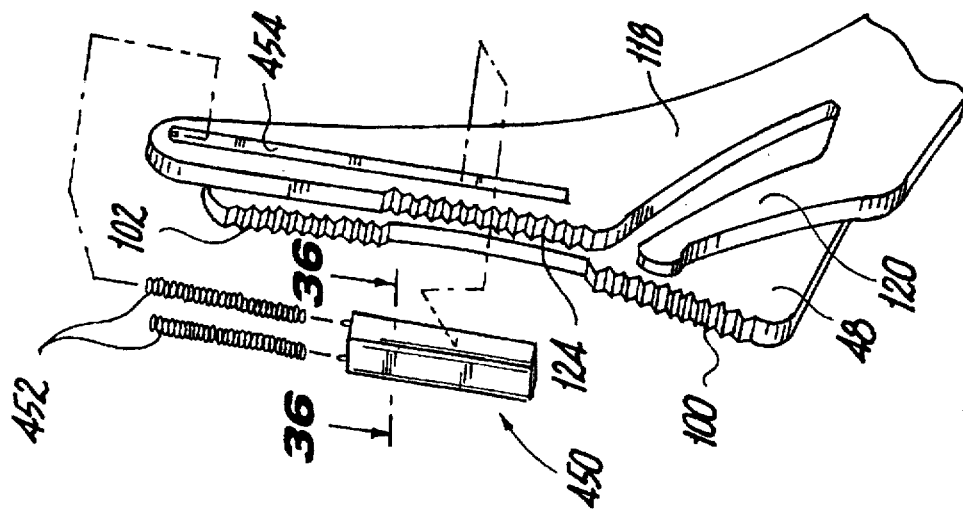

APPARATUS FOR APPLYING SURGICAL CLIPS WITH IMPROVED JAW AND CLOSURE MECHANISMS

CROSS REFERENCES

This application is a Continuation-in-Part of U.S. application Ser. No. 08/134,347 filed on Oct. 8, 1993, now U.S. Pat. No. 5,607,436.

BACKGROUND OF THE INVENTION

1. Field of the Invention

This invention relates to an apparatus for applying surgical clips to body tissue during laparoscopic or endoscopic procedures, and more particularly, to an improved surgical clip applier adapted to apply fully crimped clips as well as partially formed clips during surgical procedures.

2. Description of Related Art

In laparoscopic and endoscopic surgical procedures, a small incision is made in the patient's body to provide access for a tube or cannula device. Once extended into the patient's body, the cannula provides an access port which allows insertion of various surgical instruments through the cannula for acting on organs, blood vessels, ducts or body tissue far removed from the incision. Often during these procedures, it is necessary to apply hemostatic clips to blood vessels or various ducts to prevent the flow of body fluids therethrough during the procedure. Many times, the surgical procedure may necessitate the temporary implantation of shunts or tubes into ducts or vessels. Such procedures, such as gall bladder surgery, often require the placement of a shunt into the ducts during excision of the organ. To secure the shunt, a clip must be applied which is partially closed so as to avoid occluding the shunt.

One clip applier known well in the art is described in U.S. Pat. No. 5,084,057. This instrument includes a mechanism for sequentially advancing a plurality of surgical clips towards a pair of distal jaw members. Through actuation of handle structure, the jaw members are closed to advantageously crimp the clip.

It has been common for clip appliers to rely on friction to capture a clip between the jaw members following advancement of the clip from the clip supply. Accordingly, the jaw members are constructed so as to have a gap between the crimping surface of each jaw member which is slightly less than the distance between the legs of a clip, so that the clip is slightly pinched between the jaws to hold the clip therein. However, friction alone does not provide the reliability and security necessary to capture clips during operation.

The jaw members are typically a costly item since they are machined from a single piece to form the crimping surfaces. In view of this, it has been known to fabricate the jaw members separately, and then to assemble the jaw mechanism in the clip applying instrument. However, in instruments such as those disclosed in U.S. Pat. Nos. 5,047,038; 4,246,903 and 4,228,895, the jaws are hinged at a pivot point and do not provide reliable securements and accurate camming. Should the jaw members be improperly gapped or aligned, the clip tends to fall out of the jaws, and potentially, into the patient's body. In addition, the clip advancement mechanism may not properly orient the clip if the jaws are not properly spaced.

There is a need for an improved clip applicator which may be used in endoscopic or laparoscopic procedures such as gall bladder operations which is configured so that partial closure of a clip during the procedure can be reliably conducted. In addition, a need exists for a clip applier which accurately advances, holds a clip in the jaw mechanism without damaging tissue and applies a clip reliably and which prevents splaying of the jaws in the event of a clip over clip application. An instrument is also needed which provides the ability to apply differently shaped clips. An instrument is also needed which prevents accidental feeding of a clip or accidental return of the trigger.

SUMMARY OF THE INVENTION

A novel clip applier of the present invention obviates the disadvantages encountered in the prior art and provides a reliable and safe instrument which ensures accurate and efficient application of clips during a surgical procedure. The clip applier of the present invention provides an instrument which allows the surgeon to apply either fully or partially closed clips having various shapes during a gall bladder operation to permit securement of shunts in organs without occluding the shunts, and provides means for choosing between one mode for a full closure of jaws and the other mode for a partial closure of jaws to the predetermined amount. The instrument of the present invention substantially reduces the possibility of clips inadvertently over-advancing or backsliding, retracting or falling out of the jaws, and prevents splaying of the jaws in the event a clip is applied over a previously applied clip.

In accordance with the present invention, an apparatus is disclosed for applying surgical clips to vessels and ducts in a patient which comprises a handle portion, a body portion which extends distally from the handle portion, a clip supply for storing a plurality of surgical clips, a jaw mechanism disposed at the distal end of the body portion comprising a pair of jaw members which is movable between an open position for receiving a clip and a closed position for forming a clip in response to movement of the handle portion, means for advancing a clip from the clip supply to the jaw mechanism, means for securing a clip during closure and means for ensuring completion of the closing stroke of the jaw members.

The instrument includes crimping regions disposed on each jaw member in the form of grooves particularly shaped to fit various staples, the cross section of which may be circular or angular. Such grooves enable better control and support of staples during closure. The crimping regions also include detents for reducing the eyelet size of a clip. The present invention also provides a means for preventing splaying or over-opening of the jaw members, e.g., in the event that a clip is applied over a previously applied clip at the surgical site. The present invention further provides a shrink wrap or a metal sleeve which prevents the jaws from opening further than the at-rest gap between the jaw members prior to the receipt of a clip.

The present invention also contemplates the provision of a clip engaging means to align and control a clip. Associated with the advancing means, an engaging means is disclosed for engaging the inside surface of a clip subsequent to advancing the clip to the jaw mechanism and aligning the clip between jaw members. Further, this embodiment includes a tissue stop means for contacting a vessel when the jaw members are devoid of a clip where the clip engaging means are disposed on the tissue stop means. Such clip engaging means comprises a raised wall surface on the tissue stop means. The raised wall surface has a curved leading edge so to avoid cutting of tissue. The clip engaging means may also include a plurality of raised wall surfaces engaging both inside and outside surfaces of a clip.

The present invention also provides a switching mechanism associated with said handle portion for permitting a partial closure of the jaw mechanism to a predetermined extent. The switching mechanism includes a button member and a stop member. The button member is positioned on a movable handle portion and the stop member is positioned within the body portion so that the engagement between the button member and the stop member permit a partial closure over a full stroke. Furthermore, the switching means includes a spring member and a detent member so that the detent member restraints the button member during a closure and the spring member resets the button member upon a full closure. The present invention provides the surgeon with an apparatus which will allow him to apply surgical clips to ducts within the body and further provides a means for securing the temporary implantation of shunts or tubes in ducts by allowing partial closure of a clip without fully forming the clip to prevent occlusion of the duct or implanted shunt.

An additional feature of the present invention includes a resistor mechanism positioned within the handle portion to create resistance over the closing stroke. The resistance provides a tactile indicating measure of closure. The resistor mechanism comprises a biasing means and a detent member where the detent member, positioned on a moveable handle portion, deflects the biasing means during the closing stroke. The biasing means includes an inclined surface where the detent member slides on such surface during the closing stroke.

It is also contemplated that a slide mechanism is provided to ensure completion of the closing stroke. The slide mechanism is operatively connected to the pair of rack members arranged in a parallel relationship. The first rack includes teeth over at least a partial closing distance at both ends and does not provide teeth for a portion of the closing stroke. The second rack member, positioned next to the first rack member, will include teeth over the distance in which the first rack member is devoid of teeth. These rack members are engaged by a pawl member positioned on the movable handle portion during the closing stroke. The slide mechanism comprises a cover member slidable on the second rack member and biased by a spring against the direction of the pawl member during the closing stroke. The cover member prevents the pawl member from slipping backward during the closing stroke.

BRIEF DESCRIPTION OF THE DRAWINGS

The foregoing features and further features of the present invention will become more readily apparent and may be understood by referring to the following detailed description of an illustrative embodiment of the clip applying instrument, taken in conjunction with the accompanying drawings, in which:

FIG. 1 illustrates a perspective view of the clip applying instrument of the present invention;

FIG. 12 illustrates a side plan view of the tissue stop means of FIG. 11, including raised wall surfaces for engaging a clip;

FIG. 17 illustrates a plan view of the jaw members with a novel feature of a tab member supporting the clip 144 before crimping;

FIG. 18 illustrates a side cross-sectional view of the jaw members and the tab member taken along section line 18 of FIG. 17;

FIG. 19 illustrates a plan view of the jaw members in which the jaw members are in a closed position;

FIG. 35 illustrates an exploded perspective view of the slide mechanism associated with the rack members of the handle portion of FIG. 21 in which the slide mechanism includes the slide member and the spring;

FIG. 36 illustrates a cross-sectional view of the slide member taken along section line 36—36 of FIG. 35;

FIG. 37 illustrates a plan view in partial cut-away of the slide mechanism as the pawl member moves along the second rack member; and FIG. 38 illustrates a plan view in partial cut-away of the slide mechanism as the pawl member moves along the second portion of the first rack member and the slide member returns to its original position.

DETAILED DESCRIPTION OF THE PREFERRED EMBODIMENTS

Figure 2B:
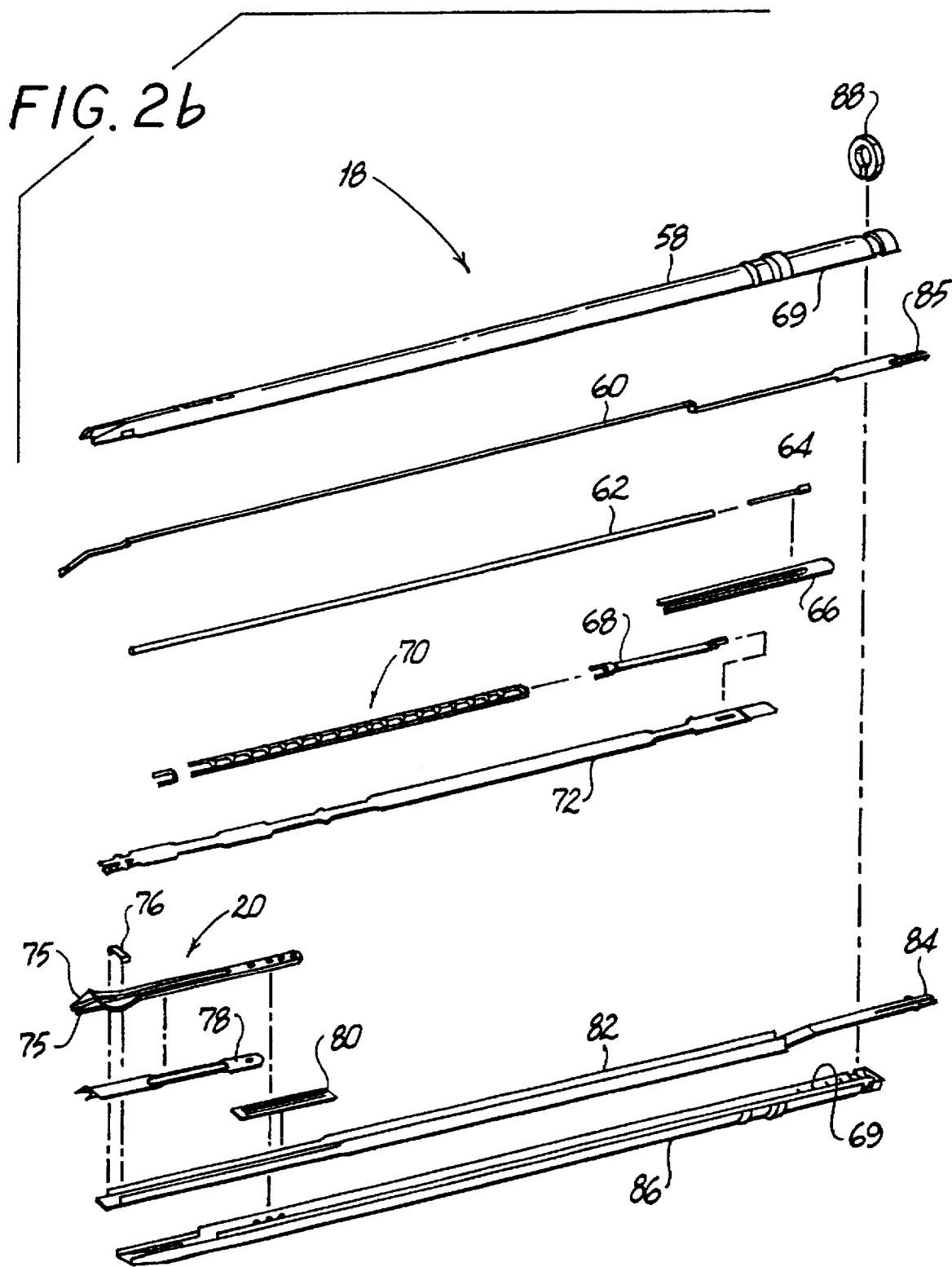
FIG. 2 illustrates a plan view of the jaw mechanism of the instrument.

Referring now in specific detail to the drawings, in which like reference numerals identify similar or identical elements throughout the views, FIG. 1 illustrates a clip applying instrument 10 of the present invention. The clip applying instrument 10 includes a handle portion 12 having a movable handle 14 and a stationary hand grip 16, which serves to operate a jaw mechanism 20 through the provision of an elongated body portion 18.

Referring to FIGS. 2–6, there is illustrated an improved embodiment of jaw members 75 with novel features of semi-circular and triangular grooves. These novel features provide a better security and support for a differently shaped clip positioned within the jaw members 75 during crimping.

Figure 3:
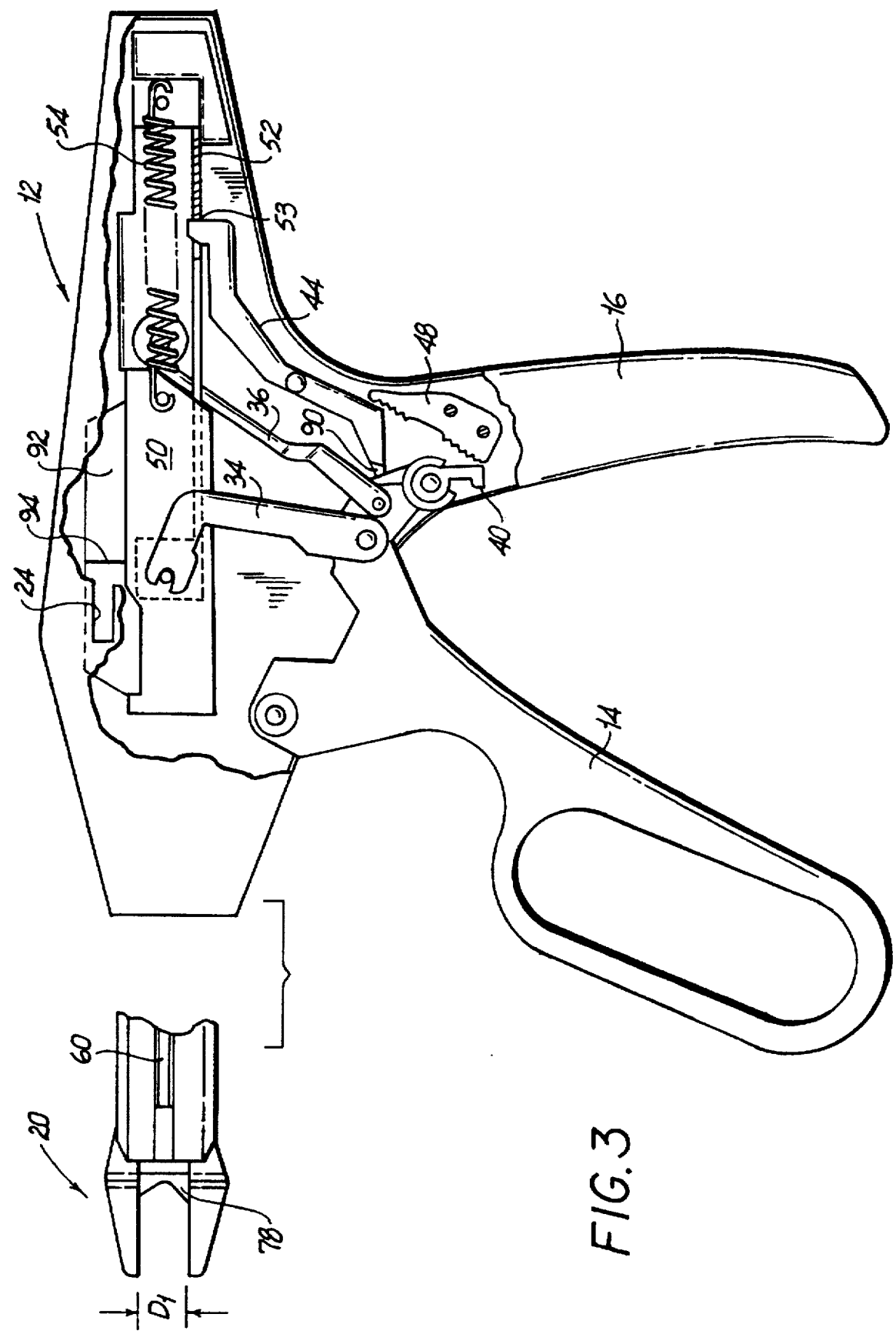
FIG. 3 illustrates a cross-sectional view of the jaw members of the jaw mechanism taken along section lines 3—3 of FIG. 2 where a clip has a round cross-section.
Figure 4:
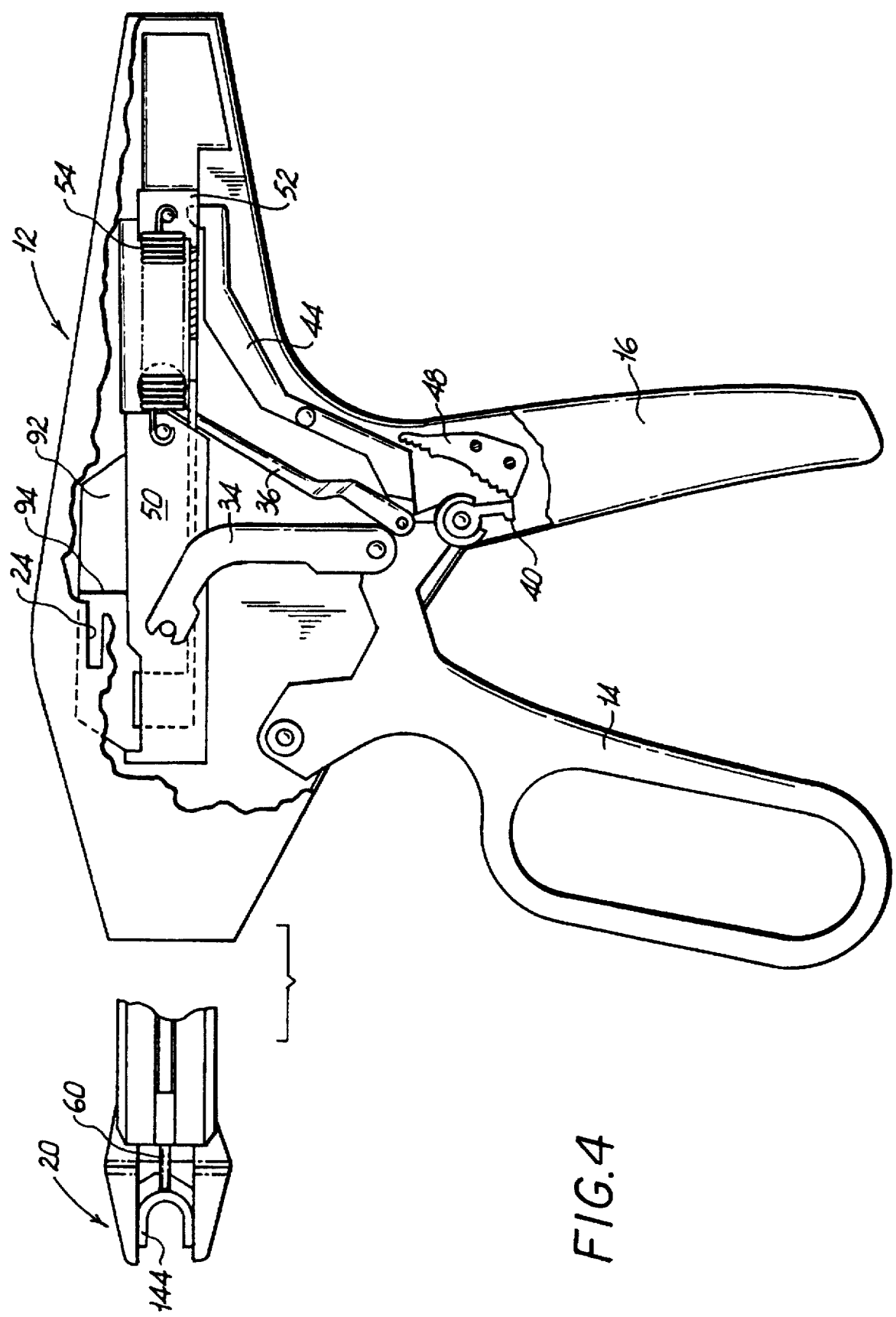
FIG. 4 illustrates a perspective view of a clip applied by the jaw members of FIG. 3.

One type of embodiment of the jaw members 75 is illustrated in FIGS. 2 and 3 for utilizing a clip such as a clip 144 illustrated in FIG. 4. Referring to FIG. 2, the jaw mechanism 20 is at its initial at-rest position prior to the crimping of a clip positioned within the jaw mechanism 20. In this initial at-rest position, the jaw members 75 are spaced to receive the clip 144 therebetween. The inside edge of each jaw member 75 provides clip securing regions 400 where the clip 144 is formed, upon closure. As shown in FIG. 3, the clip 144 has a circular cross section 404, and accordingly, the jaw members include the clip securing regions 400 having semicircular grooves 402 extending longitudinally thereon so that at least an outer surface of the clip 144 abutting jaw members 75 is arrested and supported by the semicircular grooves 402. The perspective view of the clip 144 in FIG. 4 illustrates a circular cross-section of the clip 144 as well.

Figure 5:
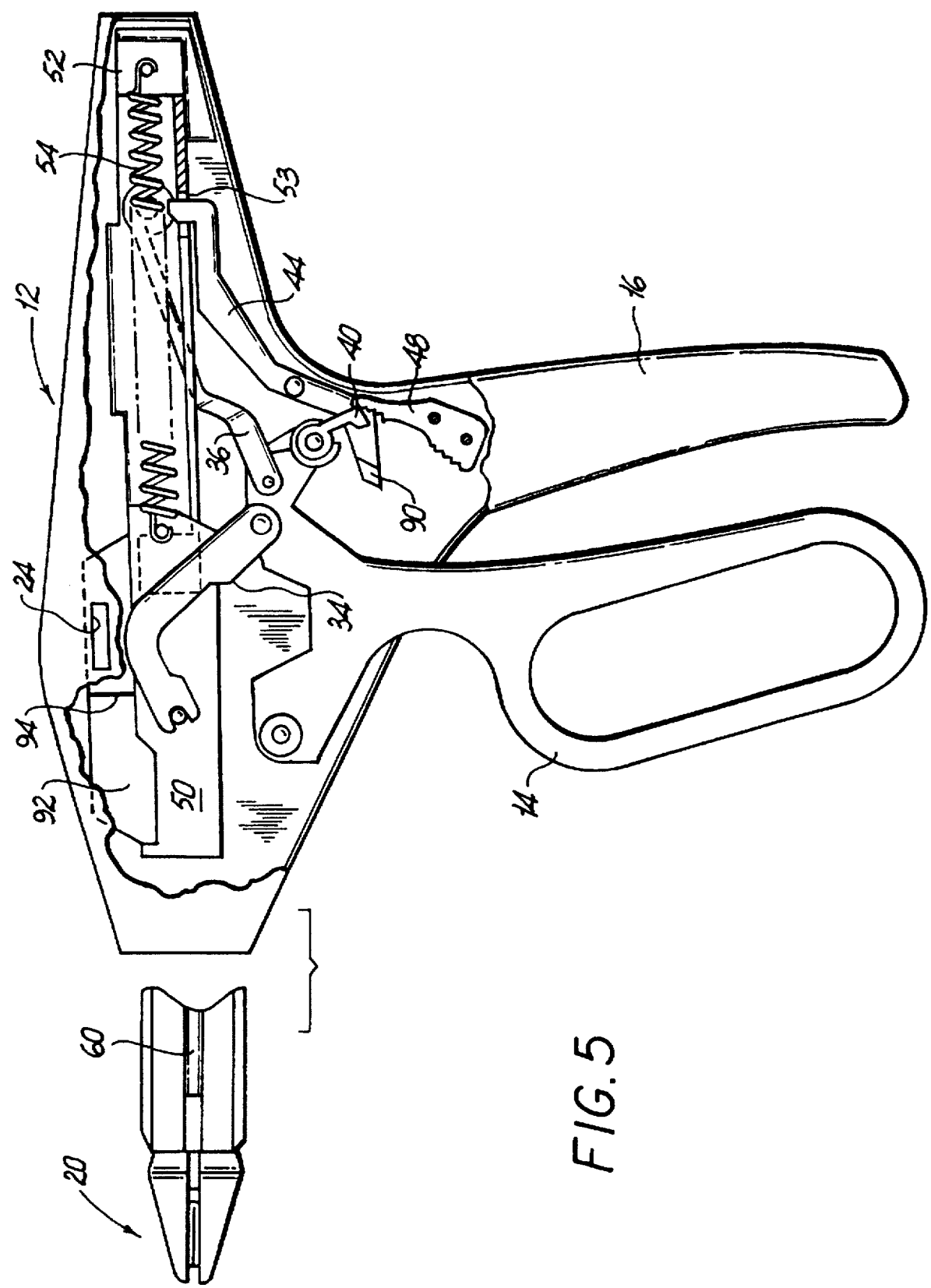
FIG. 5 illustrates a cross-sectional view of the jaw members of the jaw mechanism taken along section line 3—3 of FIG. 2 where a clip has a triangular cross-section.
Figure 6:
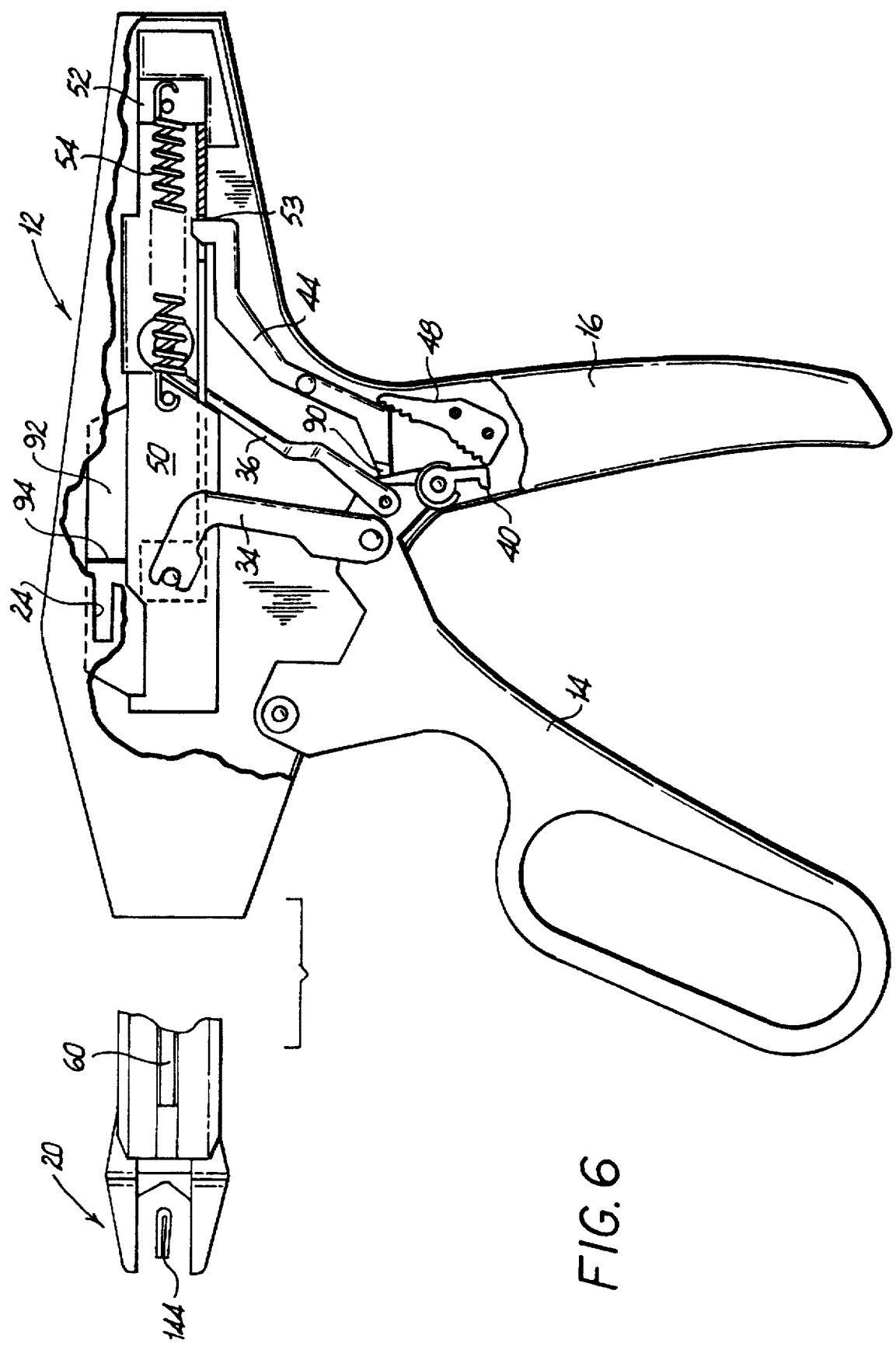
FIG. 6 illustrates a perspective view of a clip applied by the jaw members of FIG. 5.

Another embodiment of the jaw member 75 is illustrated in FIGS. 5 and 6. Referring to FIG. 5, the jaw mechanism 20 is at its initial at-rest position with the jaw members 75 spaced to receive a clip 144a. As shown in FIG. 6, the clip 144a has a triangular cross-section 404a. Accordingly, the jaw members include clip securing regions 400a having corresponding triangular grooves 402a extending longitudinally thereon so that at least an outer surface of clip 144a abutting the jaw members 75 is arrested and supported by the triangular grooves 402a.

Figure 7:
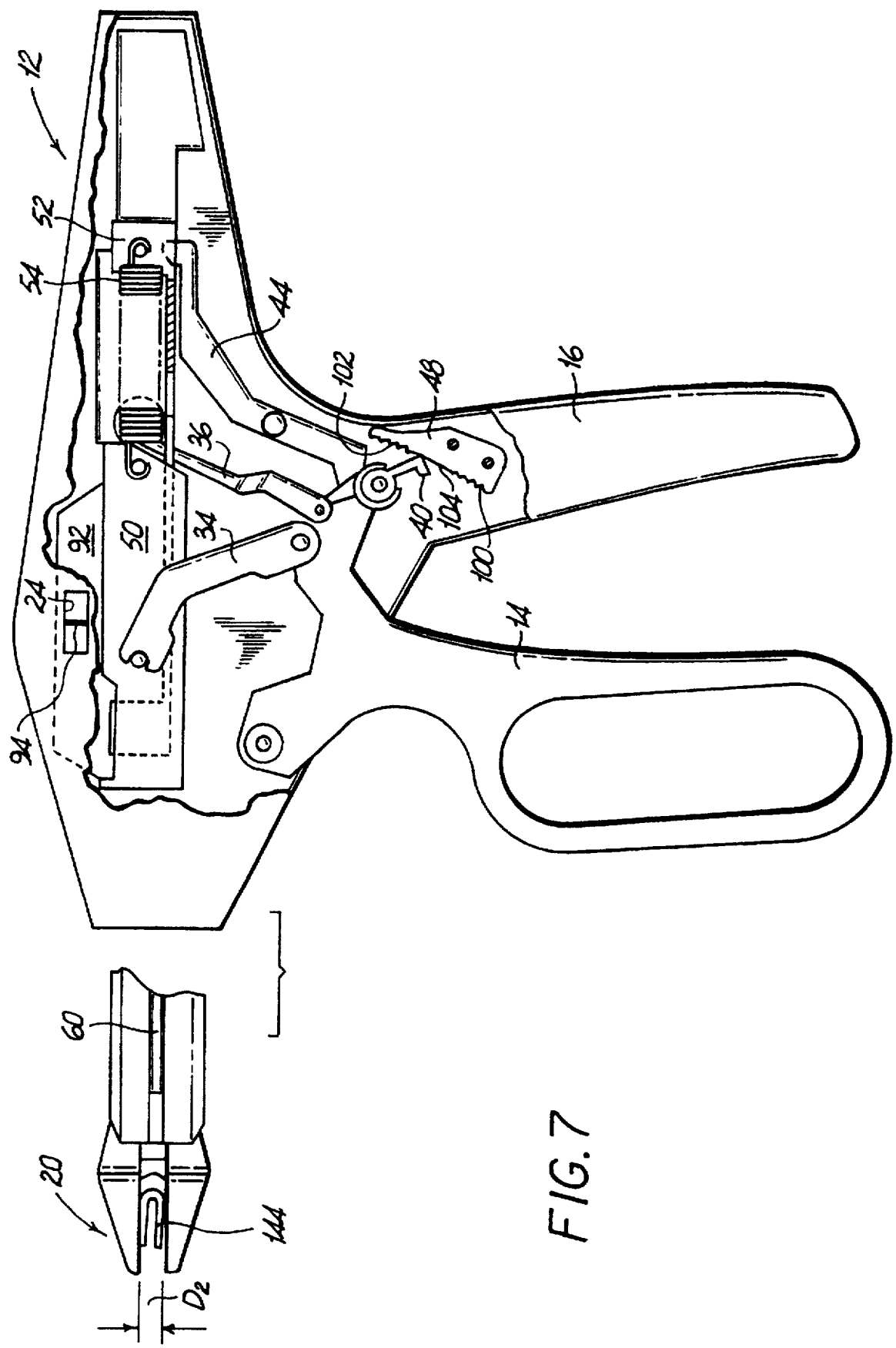
FIG. 7 illustrates a plan view in partial cutaway of the jaw mechanism of the instrument of FIG. 1 having tissue between the jaw members in an open position.
Figure 8:
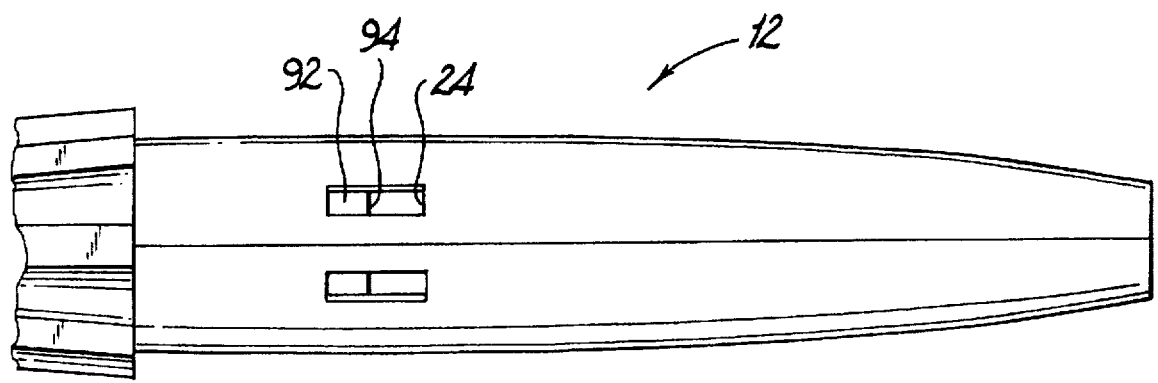
FIG. 8 illustrates a plan view in partial cutaway of the jaw mechanism of FIG. 7 crimping a clip, further illustrating the detent feature for reducing the eyelet of the clip.

FIGS. 7 and 8 illustrate a further embodiment of the jaw mechanism 20 with modified jaw members. Referring to FIG. 7, the jaw mechanism is at its initial at-rest position prior to the crimping of the jaw members 75, having the clip 144 therebetween. FIG. 7 additionally illustrates detents 408, which are arcuate projections near the proximal ends of the clip securing regions 400. The detents 408 do not interact with the clip 144 at the initial at-rest position and preferably are disposed within the clip securing regions 400 so that the clip 144 would not be hindered during the advancement. The clip 144 is advanced from a clip supply disposed within the elongated body portion 18 toward distal ends of the jaw members 75. FIG. 8 illustrates the operation of the detents 408 upon the closure of the jaw members 75. In forming the clip 144, the detents 408 reduce the eyelet size of the clip 144 and aids in clip security. Furthermore, the detents 408 provide more contact with the clip 144 and prevent backsliding of the clip by supporting the proximal end of the clip.

Figure 9:
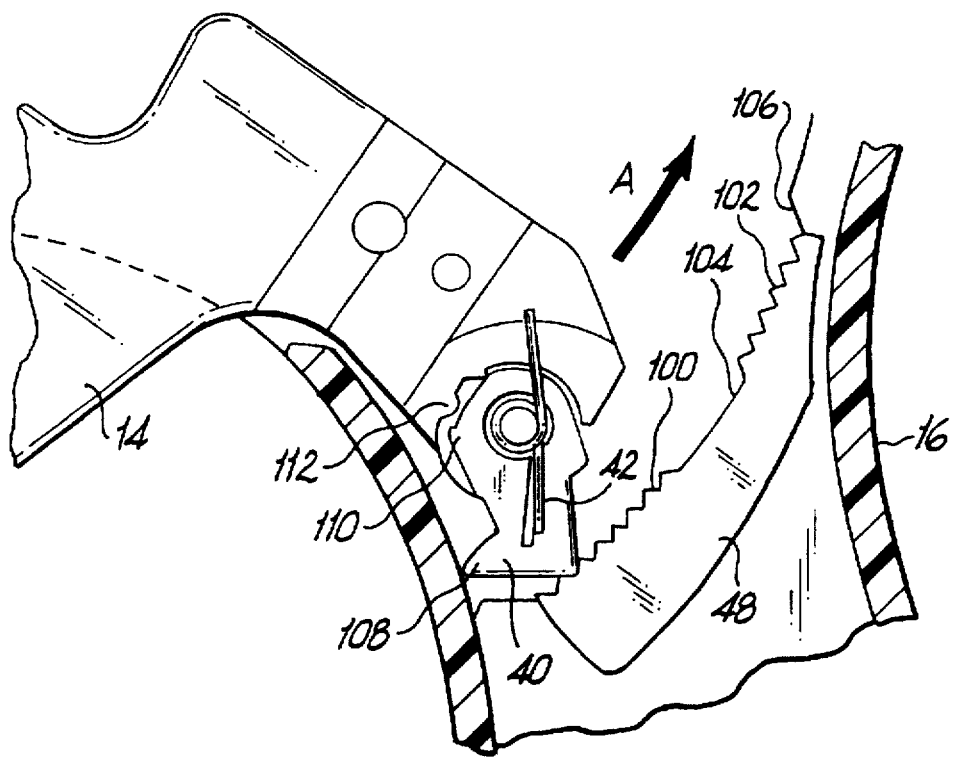
FIG. 9 illustrates an exploded perspective view of the jaw members of the instrument of FIG. 1 showing a metal sleeve for surrounding the jaw members.
Figure 10:
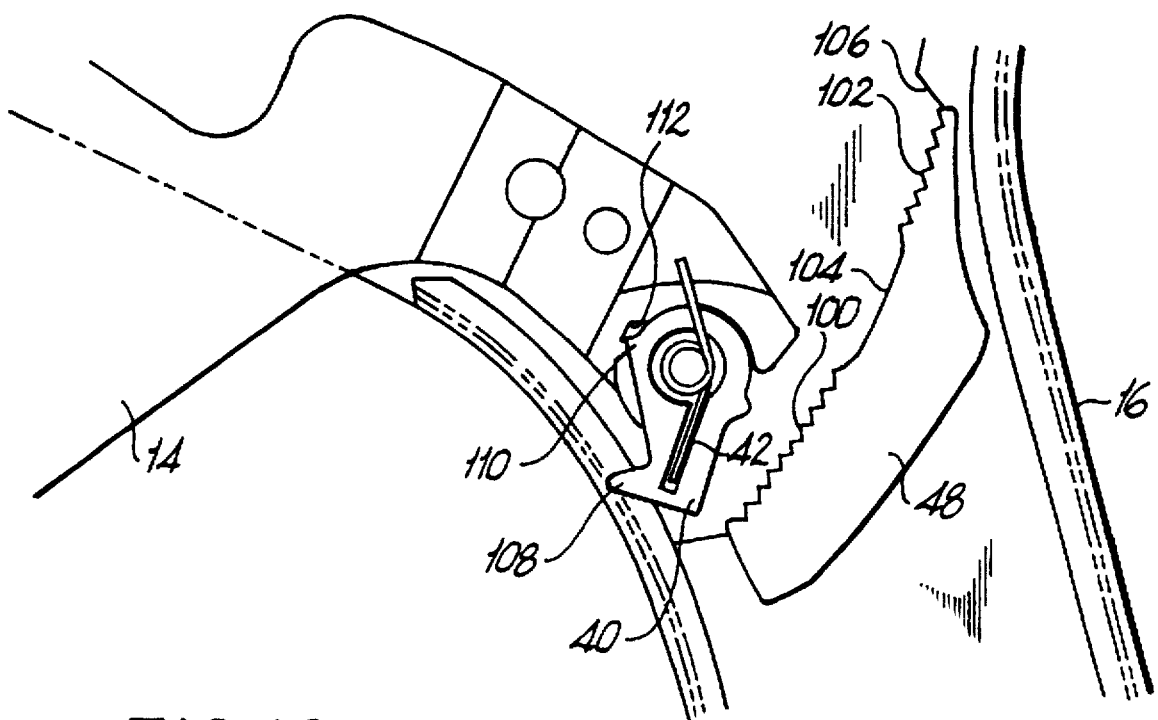
FIG. 10 illustrates a top view of the jaw members of the jaw mechanism of FIG. 9 showing the use of shrink wrap for surrounding the jaw members.
Figure 11A:
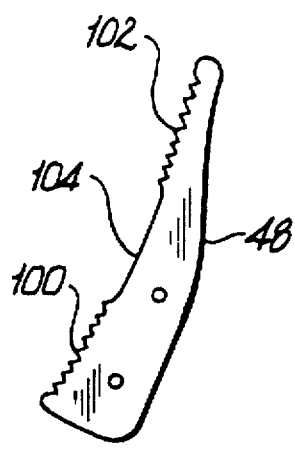
FIG. 11 illustrates a perspective view of the tissue stop means having a clip stop means of the present invention thereon.
Figure 11B:
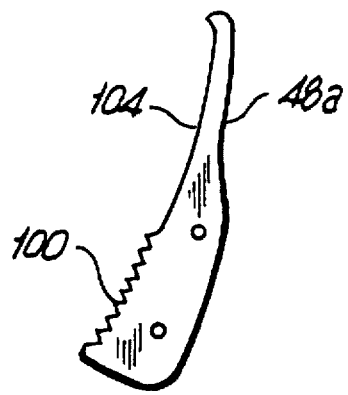
Figure 11C:
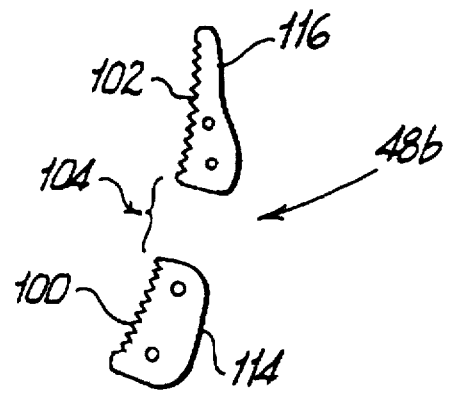
Figure 11D:
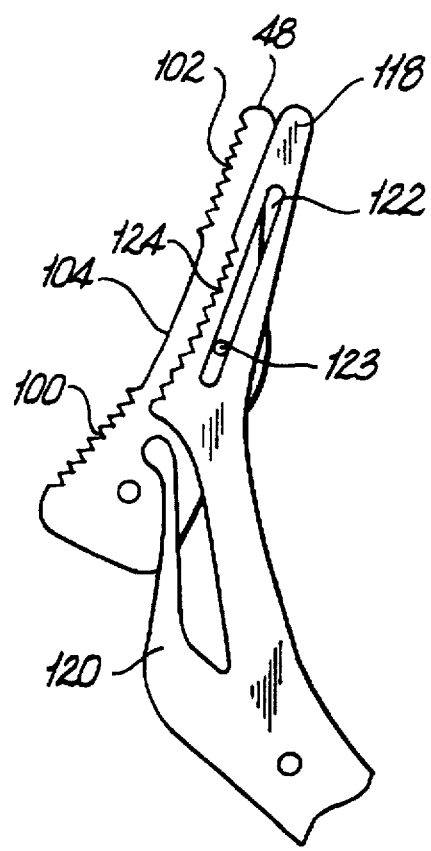
Figure 13A:
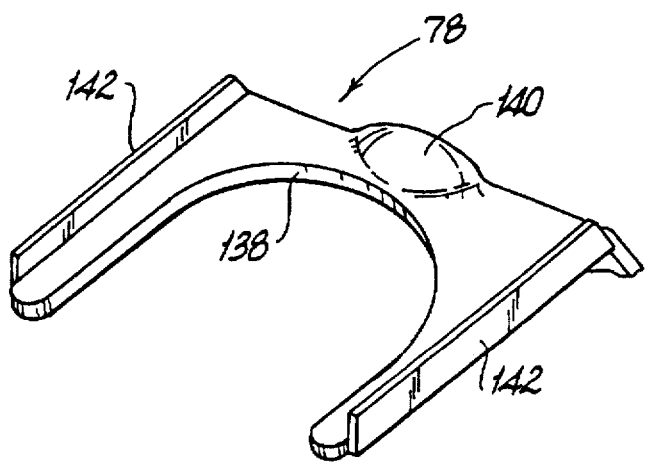
FIG. 13 illustrates a front view of the tissue stop means of FIG. 11.
Figure 13B:
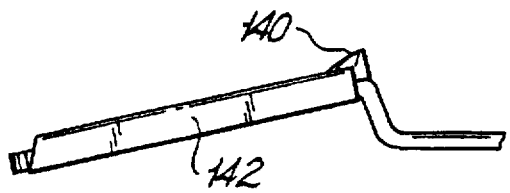
Figure 13C:
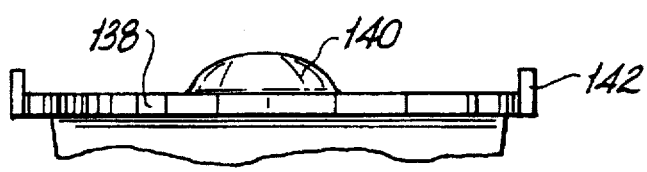

FIGS. 9 and 10 illustrate an improved embodiment of the jaw mechanism 20 with novel features of a metal sleeve 410 and a shrink wrap 412. These features provide added support to hold the individual jaw members 126 and 128 together and prevent splaying of the jaw members 126 and 128 as described below.

Turning now to FIG. 9, there is illustrated the jaw mechanism 20 including the provision of the metal support sleeve 410. The jaw mechanism 20 is positioned axially within the elongate body portion 18 of the instrument 10 (FIG. 1) with other operative elements (not shown) for advancing a clip to the jaw members 75 and for camming the jaw members 75 closed to crimp a clip positioned therebetween. A pair of jaw members 126 and 128 are constructed in mirror images and include a crimping region 130 and mounting region 134. The individual jaw members 126 and 128 are secured together by a dovetail connection arrangement 132 which secures the two jaw member 126 and 128 together and provide a mounting means 136 through the provision of a space between the dove tail portions. The metal sleeve 410 of the present invention slides over the mounting region 134 of the jaw mechanism 20 and provides added support to the jaw mechanism 20 by holding together the jaw members 126 and 128. The metal sleeve 410 includes apertures passing therethrough to correspond to mounting means 136 of the mounting region 134. Referring to FIG. 10, there is illustrated the use of a shrink wrap 412. The shrink wrap 412 surrounds the mounting region 134 and provides added support to align the jaw mechanism 20 while preventing separation of the jaw members 126 and 128. The shrink wrap can be cut out so that there would be apertures passing therethrough and corresponding to the mounting means 136 of the mounting region 134.

Referring to FIGS. 11–20, there are illustrated various embodiments of an improved tissue stop 78. The tissue stop 78 includes a vessel contacting region 138 which will contact a vessel, duct or tissue in the event a clip is not positioned in the jaw mechanism. The tissue stop 78 is positioned beneath the jaw mechanism 20 so as to provide a surface for a clip when the clip is advanced to the jaw mechanism.

Referring to FIG. 11, there is illustrated an embodiment of the tissue stop 78 with a novel feature of a plurality of notches: a notch 414 disposed on the front portion of the tissue stop 78 and a notch 153 disposed on the back portion of the tissue stop 78. As shown in FIG. 12, a contoured surface 152 connects two notches 414 and 153 so as to allow notch 414 to engage the inside surface of the clip and to allow notch 153 to engage the outside surface of the clip. As a result, the notch 153 allows the clip to ride over to the position before crimping of the clip while the notch 414 prevents the clip from over advancing. During the crimping of the clip, notches 153 and 414 prevent both advancement or retraction of the clip so that the clip would be cradled within the contoured surface 152 between the notches 414 and 153.

Figure 14A:
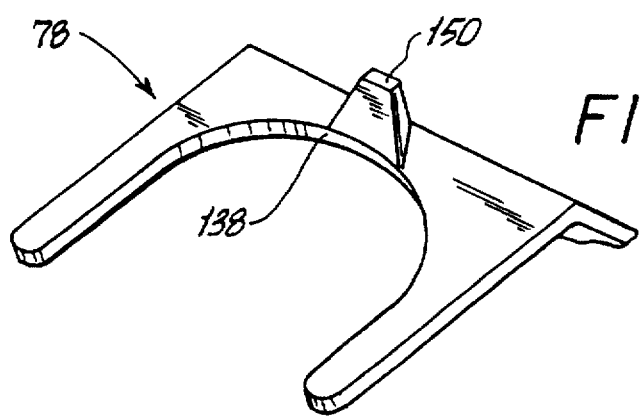
FIG. 14 illustrates the tissue stop means having another embodiment of clip stop means of the present invention.
Figure 14B:
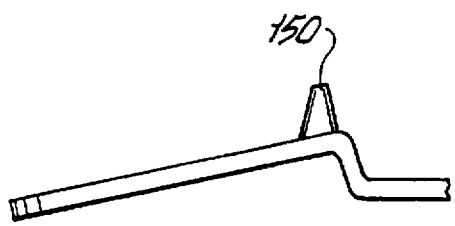
Figure 14C:
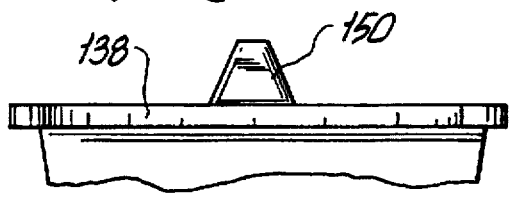
Figure 15A:
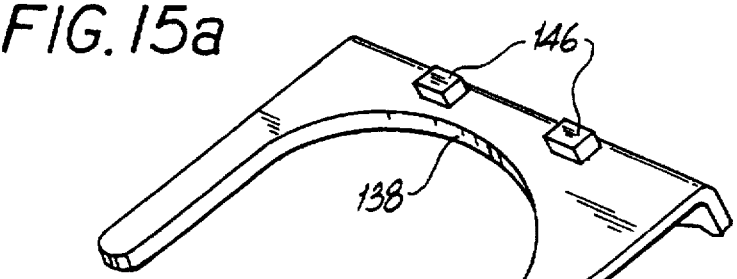
FIG. 15 illustrates a side plan view of the tissue stop means of FIG. 14 including a curved leading edge of the wall surface.
Figure 15B:
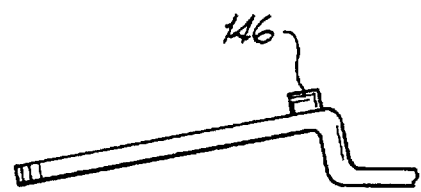
Figure 15C:
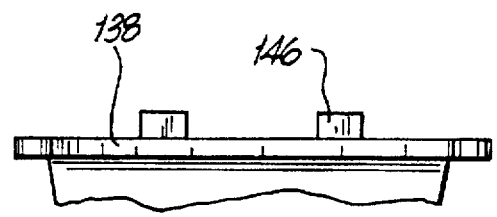
Figure 16A:
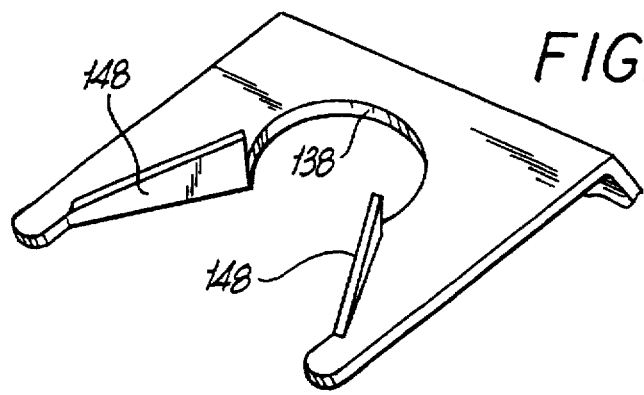
FIG. 16 illustrates a front view of the tissue stop means of FIG. 14.
Figure 16B:
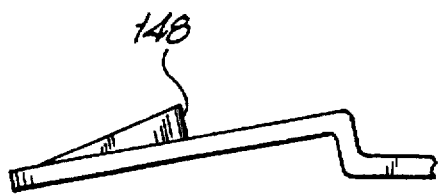
Figure 16C:
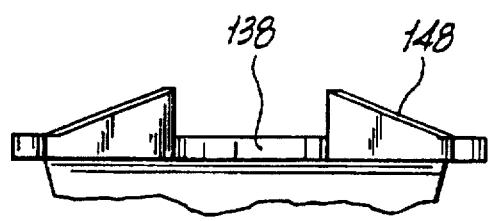

Referring to FIGS. 14, 15 and 16, there is illustrated another embodiment of the tissue stop 78 with a novel feature of a curved backwall 416 added to upstanding walls 148. The upstanding walls 148 are provided for engaging at least the inside surface of the legs of the clip as it is advanced into the jaw mechanism. The curved backwall 416 of the present invention provides radius and angles added to the upstanding wall 148 to prevent tissue from contacting sharp edges of the upstanding wall 148. The curved backwall 416 also provides further security to the clip 144 by providing more contact points than that provided by the upstanding wall 148 alone during advancement and crimping.

Figure 20:
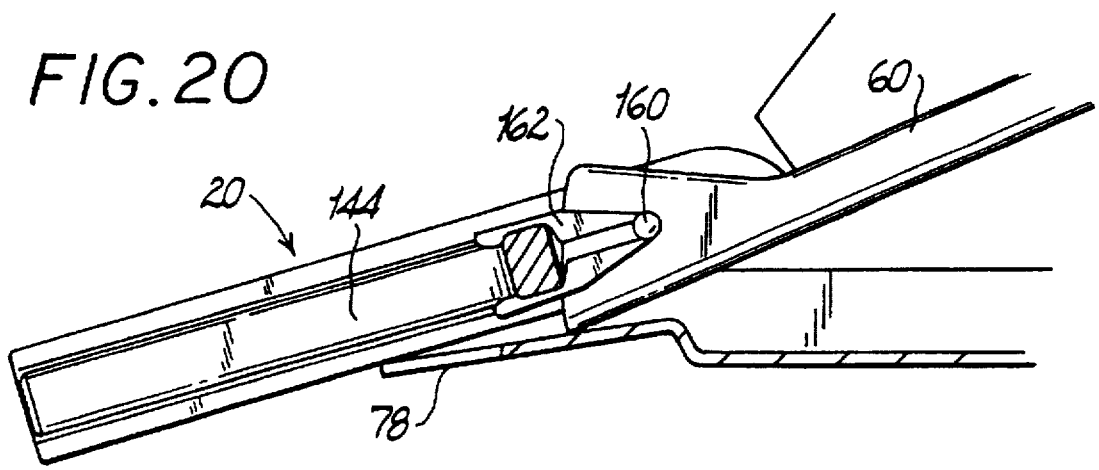
FIG. 20 illustrates a side cross-sectional view of the jaw members and the tab member taken along section line 20 of FIG. 19 when the tab member is fixed downward.

Referring to FIGS. 17-20, there is illustrated another embodiment of the tissue stop 78 with a novel feature of a tab 419 added to the distal portion of the tissue stop 78. The tab 419 is provided for contacting the inside surface of the legs of a clip to prevent backward movement of the clip 144 during crimping of jaw members 75. The curved and round surface of the tab 419 provides contact points on the clip 144 before the jaw members 75 begin to close as shown in FIGS. 17 and 18. By providing these contact points, the tab 419 prevents the clip 144 from drawing back into the jaw members. As the jaw members 75 close further, the flexible neck 419a of the clip stop 78 allows the tab 419 to bend downward and the jaw members 75 are fully closed without any interference as shown in FIGS. 19 and 20. Accordingly, jaw formation is proceeded with more control and efficiency for tighter hold of tissue.

Having thus described the improved operation of the jaw mechanism 20, reference will be made to FIGS. 21-27 which illustrate the partial crimping feature of the present invention. As discussed previously, it is often times desirable to provide a means for applying a partially closed clip during certain surgical procedures, in particular during a cholecystectomy procedure, more commonly known as gall bladder surgery. In such a procedure, it is sometimes necessary to place a shunt or tube into a duct to introduce media to the duct, while at the same time maintaining the shunt in place. Accordingly, it becomes necessary to secure the shunt in place through the application of a clip, but it is necessary to prevent occlusion of the shunt through the provision of a partially closed clip. Furthermore, since the cholecystectomy procedure has now gained increased popularity as an endoscopic procedure, the surgeon's reliance on the endoscope to determine when a clip has been partially crimped introduces additional challenges. Although the surgical site is viewed on a video monitor, the field is somewhat distorted and it may be difficult to accurately determine when the clip is partially crimped about the duct or shunt. In addition, the closing mechanism for the instrument must ensure that the partially closed clip does not disengage from the instrument prior to securement on the duct or shunt.

Figure 21:
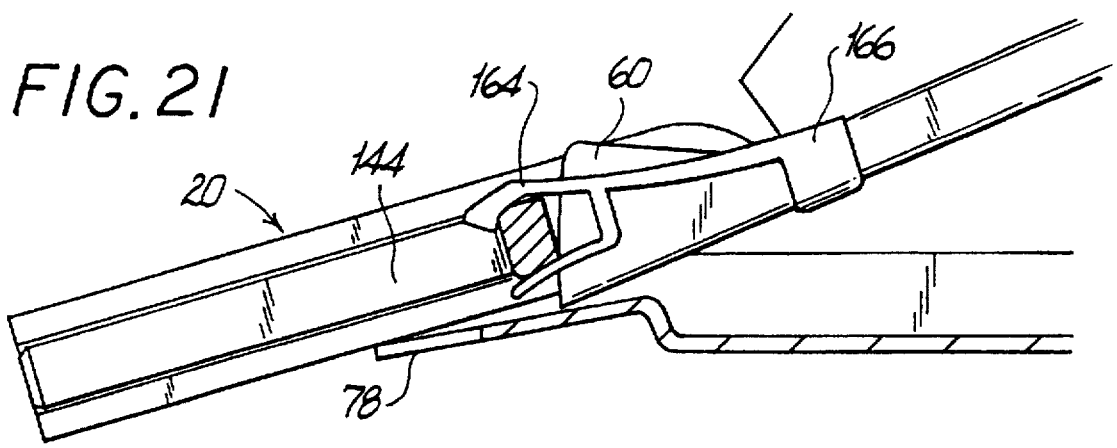
FIG. 21 illustrates a side plan view in partial cut-away of a prior art handle of the instrument of FIG. 1 in which a clip is loaded into the jaw mechanism.
Figure 22:
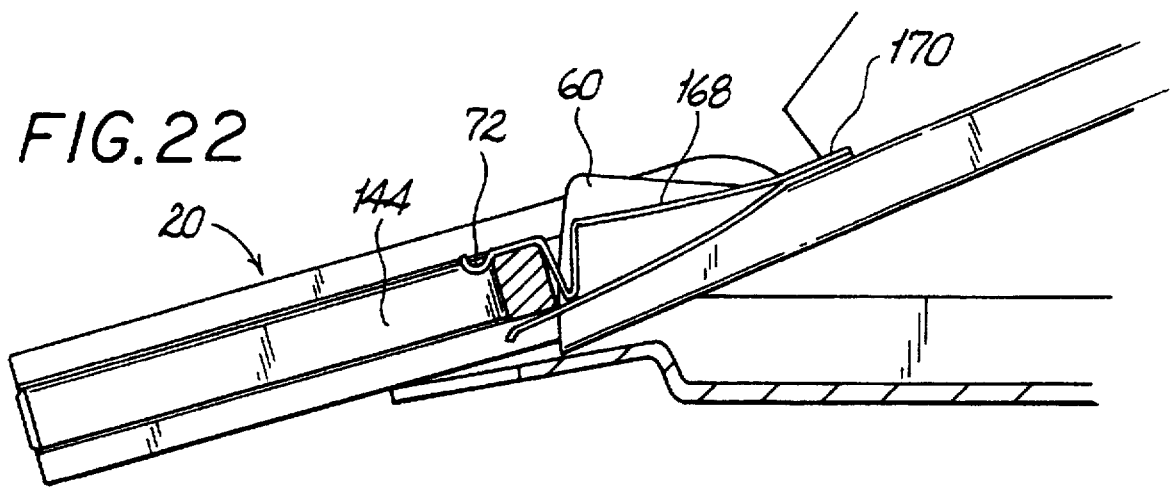
FIG. 22 illustrates a side plan view in partial cut-away of the handle of FIG. 21 in which the jaw mechanism is in a predetermined position indicative of a partial closing stroke to partially crimp a clip positioned in the jaws.

FIGS. 21 and 22 illustrate operations of the handle mechanism of the instrument 10. FIG. 21 shows the movable handle 14 of the instrument 10 substantially in the at-rest position with a clip advanced to the jaw mechanism 20. As seen in FIG. 22, as a full closing stroke of the movable handle 14 is effected towards the stationary hand grip 16, channel tube 50 is advanced through the provision of channel tube link 34. The channel tube link 34 is operatively connected so as to close jaw mechanism 20 upon the advancement of the channel tube link 34. A button mechanism as described below, provided in the present invention partially forms the clip by allowing only a partial closing stroke of the movable handle 14 and, thus, stopping advancement of the channel tube 50 at a predetermined distance.

Figure 23A:
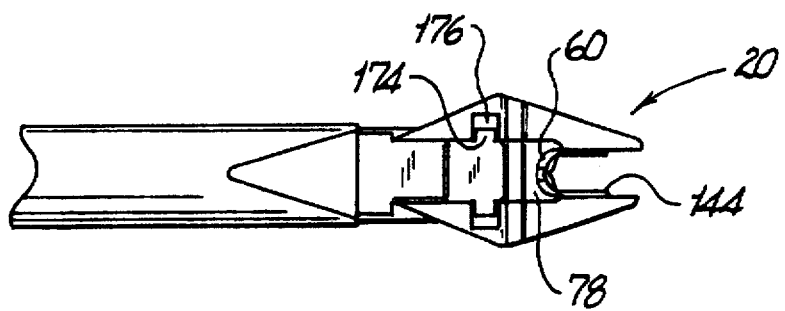
FIG. 23 illustrates a perspective view in partial cut-away of a switching mechanism associated with the handle portion.
Figure 23B:
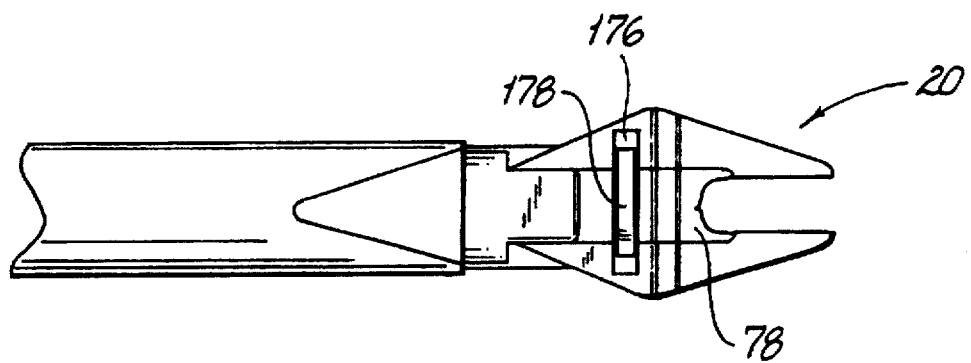
Figure 24:
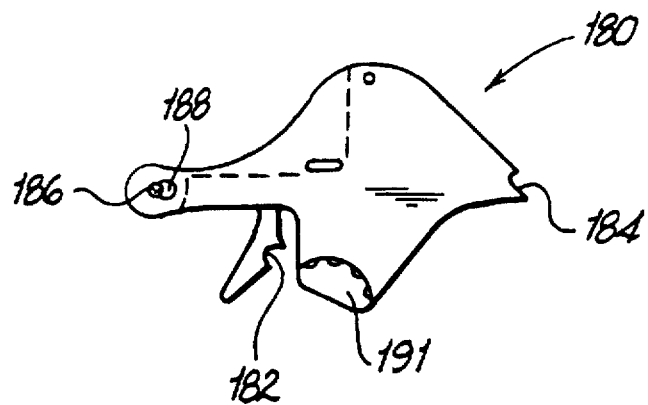
FIG. 24 illustrates a back view of the switching mechanism of the present invention showing a button member connected to a pin member taken along section line 24 of FIG. 23.
Figure 25A:
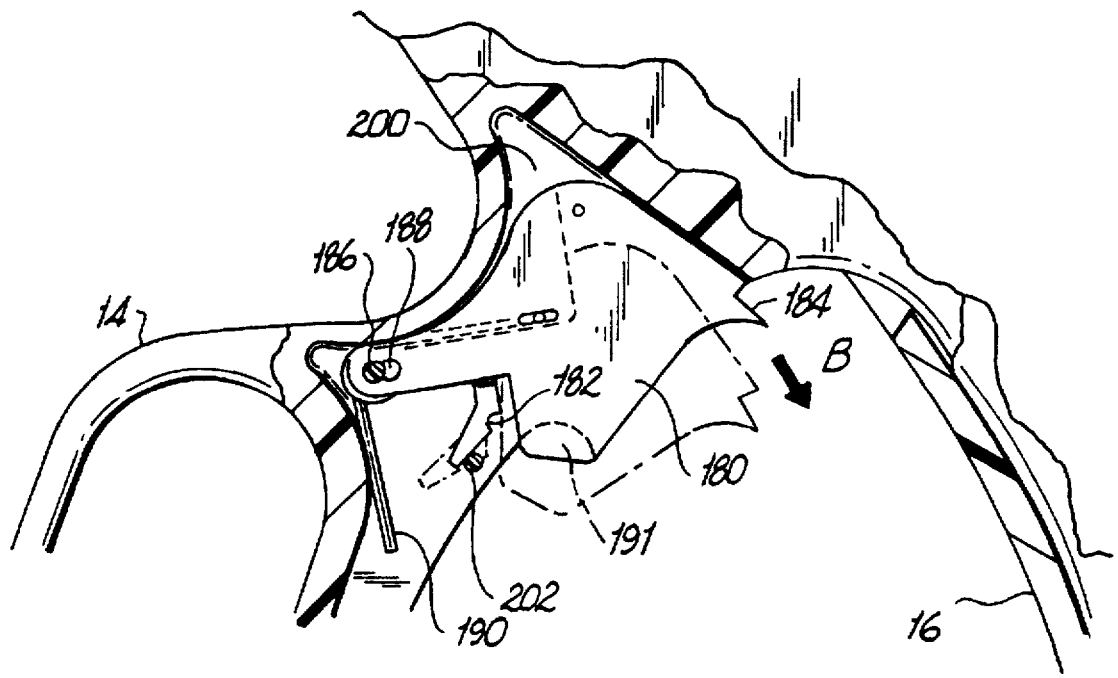
FIG. 25 illustrates a perspective view in partial cut-away of the switching mechanism showing the stop member positioned within the body portion of the instrument of FIG. 1.
Figure 25B:
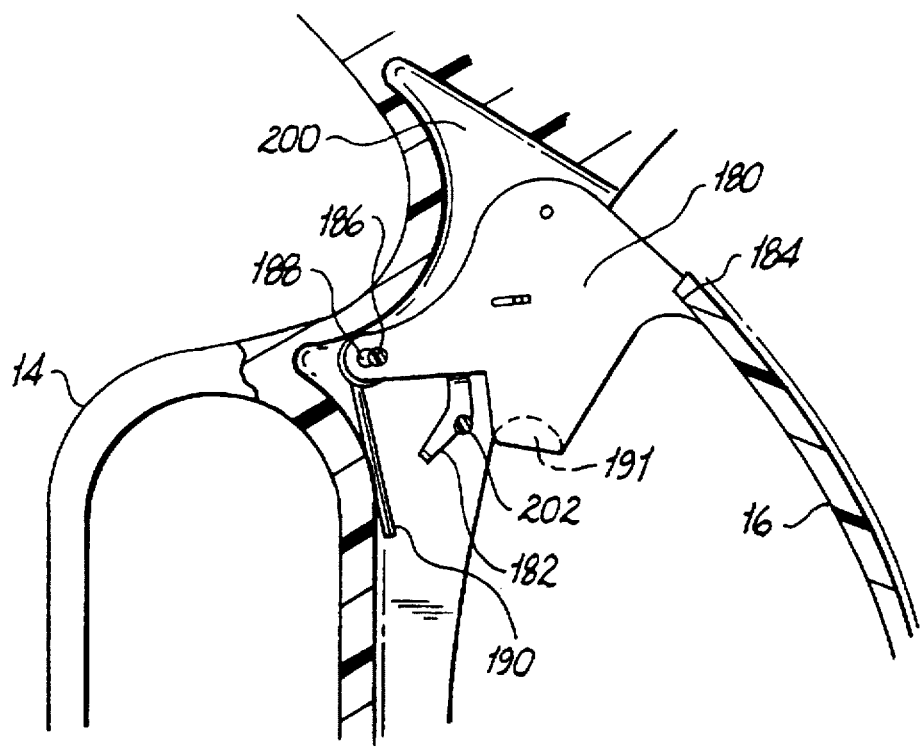
Figure 26A:
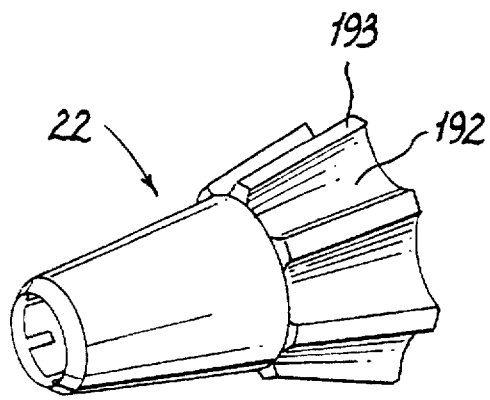
FIG. 26 illustrates a plan view in partial cut-away of the switching mechanism when the button member is depressed.
Figure 26B:
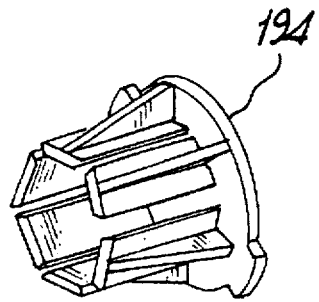
Figure 26C:
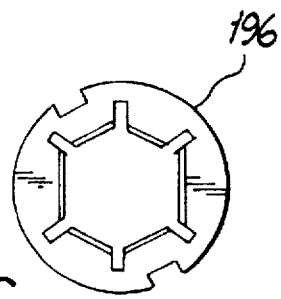

Referring to FIG. 23, there is illustrated the button mechanism 420 that provides two modes of operation: a full crimping mode and a partial crimping mode. The button mechanism 420 is disposed within hollow of the movable handle 14 where a pin 31 provides for pivoting movement of the movable handle 14. The button member 422 is connected to a pin member 424 so that the movement of the pin member 424 causes respective movement on the part of the button member 422. FIG. 25 illustrates a stop member 426 fixed to the inside wall of the stationary handle in the handle portion 12. FIG. 26 shows the respective positions of the button member 422, pin member 424 and stop member 426 at the initial at-rest stage of the button mechanism. The spring member 428 is also introduced where the spring member 428 is biased against the button member 422. The spring member 428 holds the movable handle 14 in position. As shown by the direction of the arrow in FIG. 26, the button member 422 is slightly effected toward the movable handle 14 by the user and the spring member 428 is depressed against the wall of the movable handle 14. The pin member 424 connected to the button member 422 moves in the respective direction of the button member 422. In this process, the pin member 424 rides over a detent member 430, which is another novel feature associated with the button mechanism 420. At this point the button member 422 and the pin member 424 are locked at this position by the deflected spring member 428 and the detent member 430.

Figure 27:
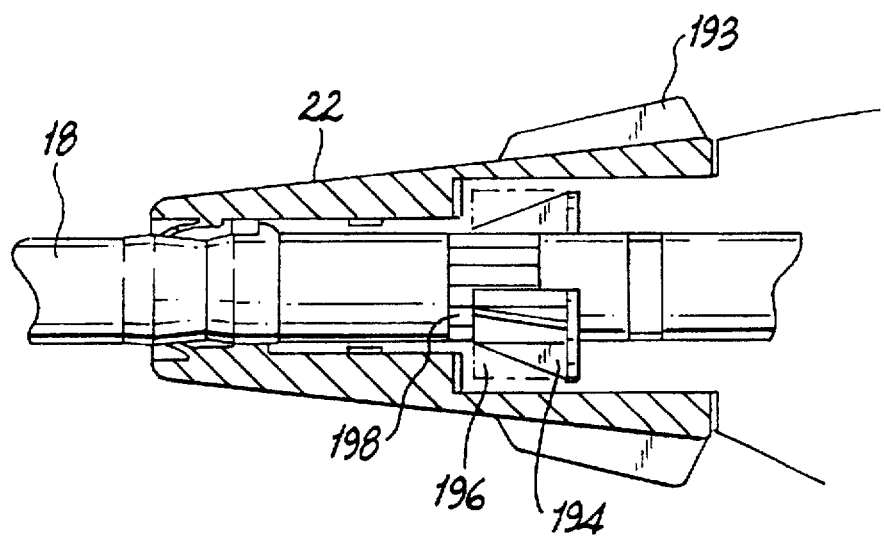
FIG. 27 illustrates a plan view in partial cut-away of the switching mechanism showing the position of the spring member and the detent member during closing stroke.

Referring to FIG. 27, there is illustrated the interaction between the pin member 424 and the stop member 426 as the closing stroke of the movable handle 14 is effected toward the direction of the arrow as shown. The rotational movement of the movable handle 14 in respect with the pin member 31 brings the button mechanism upward inside the handle portion 12. Particularly, the pin member 424 now interacts with the stop member 426. The stop member 426 prevents further upward movement of the pin member 424 and directs the pin member to the path along the bottom surface of the stop member 426. The prevention of further upward movement of the pin member 424 by the stop member 426 prevents any further pivotal movement by the movable handle 14 and, accordingly, any distal movement of the tube member 50 to completely close the jaw members. As a consequence, the closure of the jaw members is stopped in the predetermined position corresponding to a partial crimping of the clip.

Figure 28:
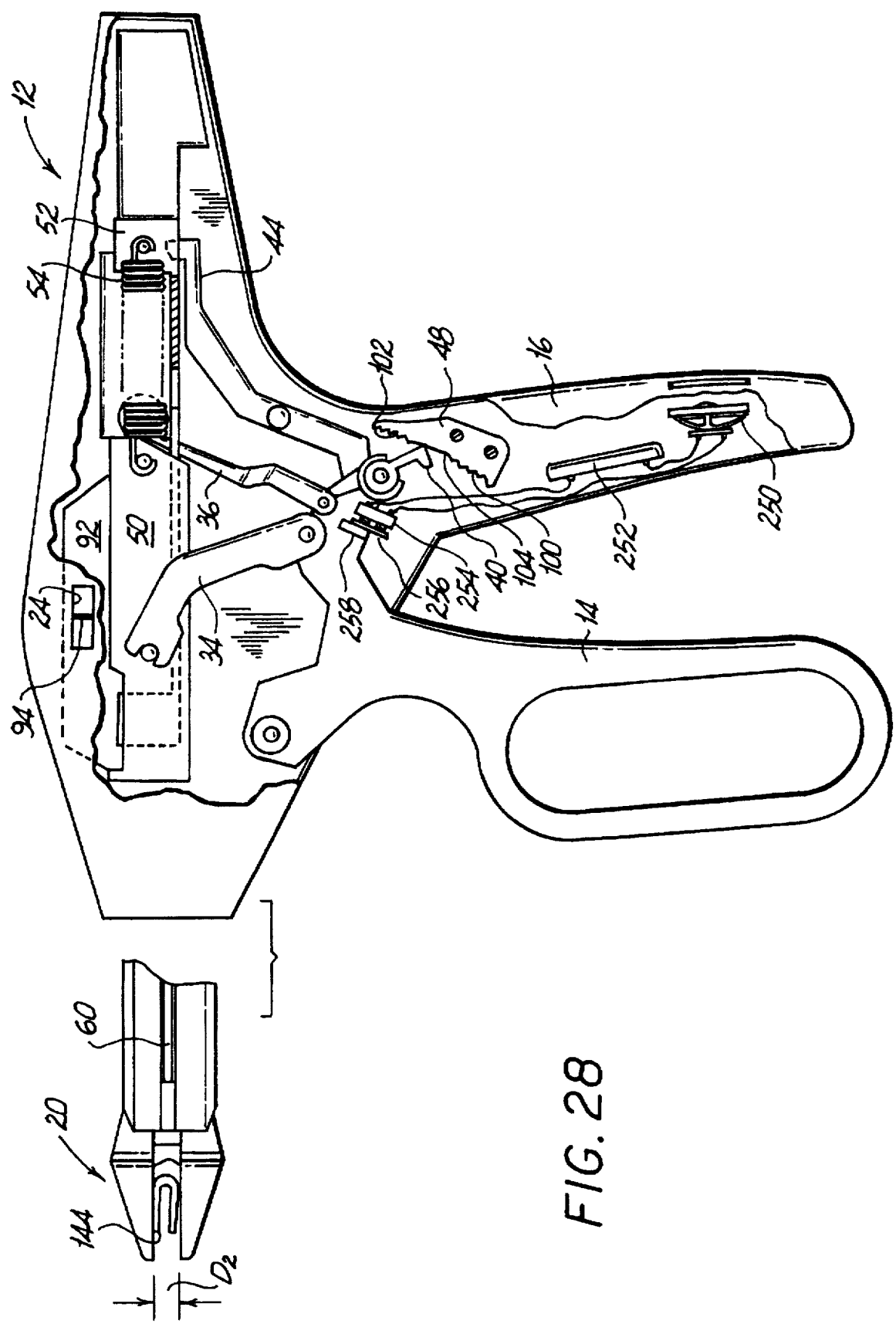
FIG. 28 illustrates a plan view in partial cut-away of the switching mechanism of FIG. 27 showing the position of the spring member and the detent member upon completion of the closing stroke.

FIG. 28 illustrates resetting of the button mechanism. The force applied by the user to the movable handle 14 is transmitted by the stop member 426 and drives the pin member 424 to ride over the detent 430. As a result, the button member 422 is released and reset to the original position. This button mechanism offers advantage by eliminating the need to check the degree of closure by visual or audio indication. When the button member is not depressed, the instrument 10 is used for a full closure of the clip.

FIGS. 29-34 illustrate the operation of a resistor mechanism 440. The resistor mechanism 440 provides a means for a user to feel tactile indication of completion of a closure while preventing accidental activation of the feed mechanism of a clip. The resistor mechanism 440 is positioned inside the handle assembly of the instrument 10 of FIG. 1 so as to provide resistance against closure movement of the movable handle 14. The resistor mechanism 440 includes a cone 442 disposed on the movable handle 14. The resistor mechanism 440 further includes a resistor 444 for a biasing means and a resistor pad 446 both of which are disposed on the stationary hand grip 16.

Figure 29:
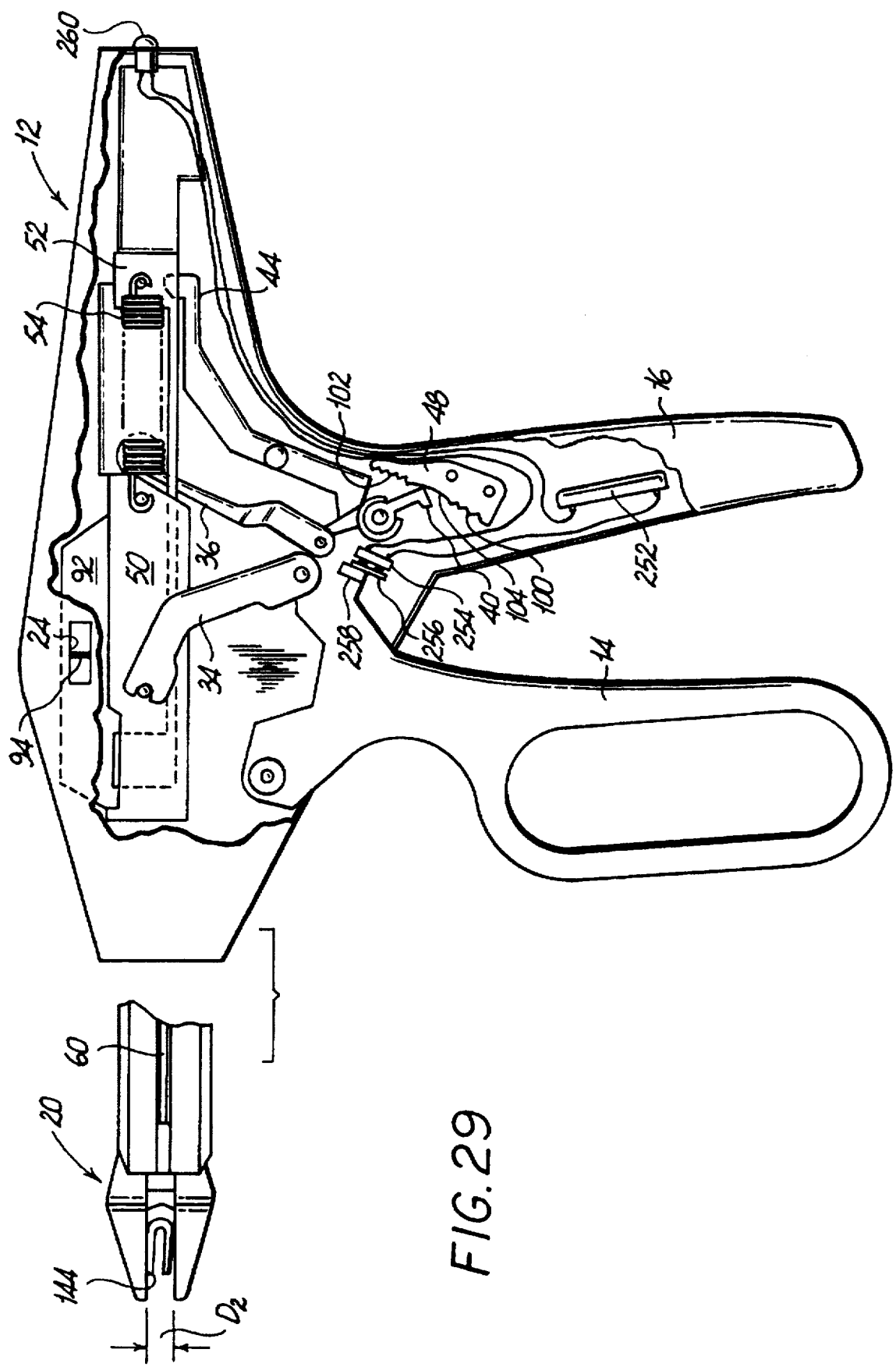
FIG. 29 illustrates a plan view in partial cut-away of a resistor mechanism showing the resistor and the cone.
Figure 30:
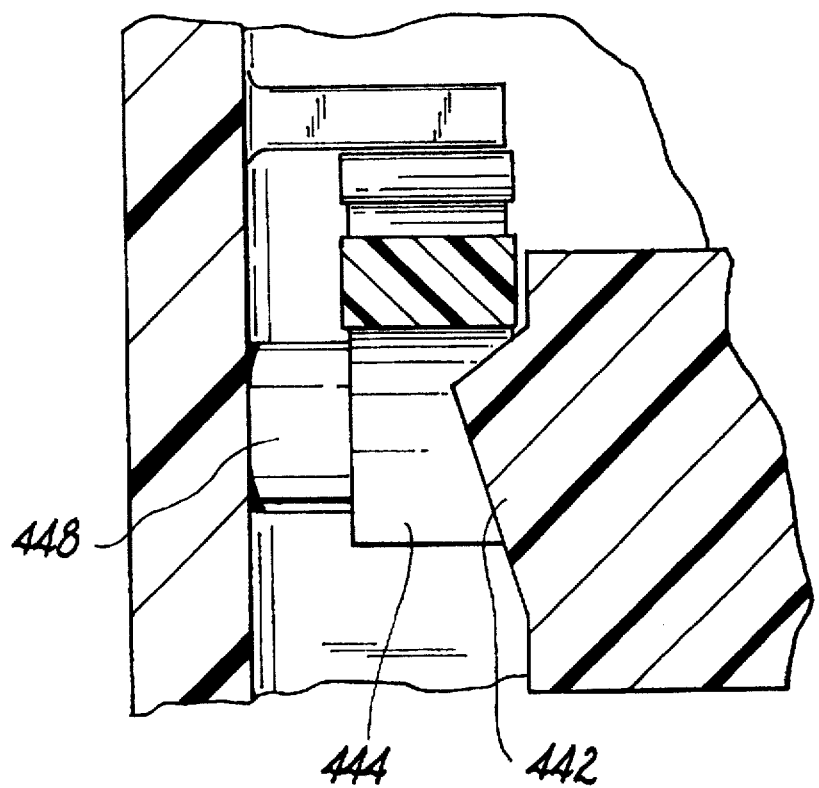
FIG. 30 illustrates a cross-sectional view of the resistor mechanism taken along section line 30—30 of FIG. 29.
Figure 31:
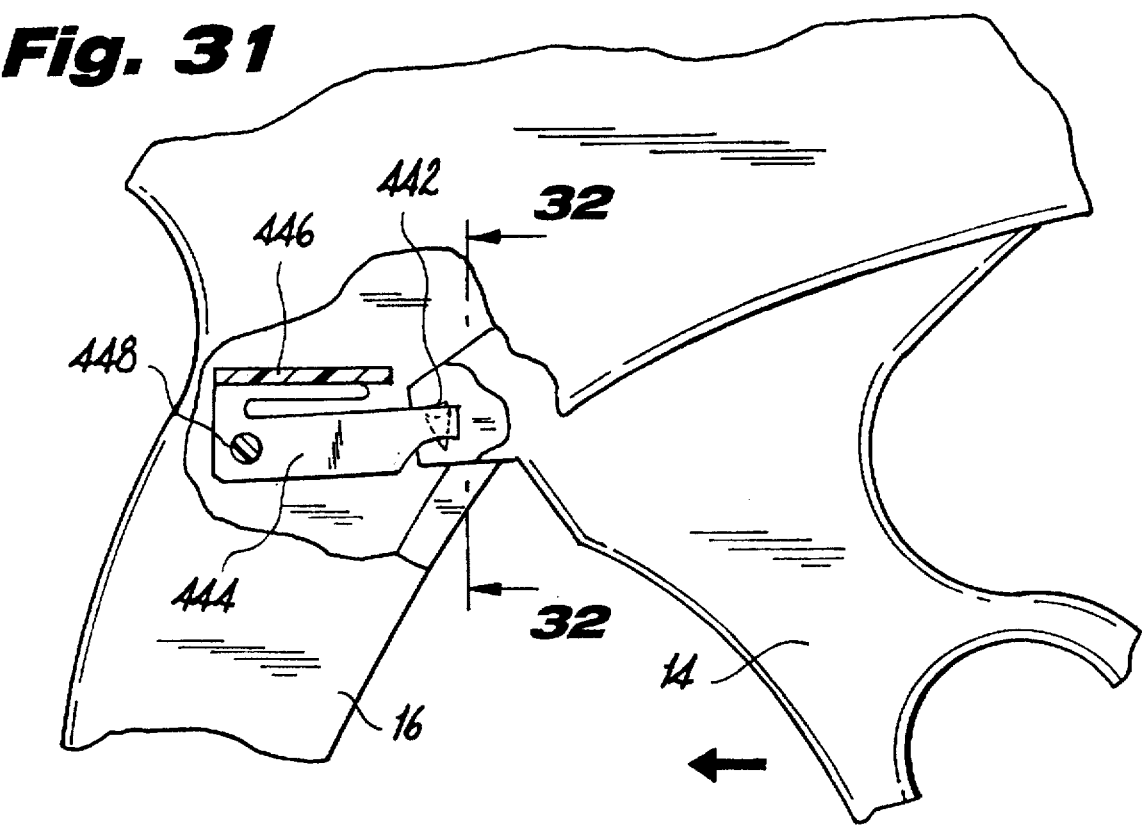
FIG. 31 illustrates a plan view in partial cut-away of the resistor mechanism of FIG. 29 during the closing stroke.
Figure 32:
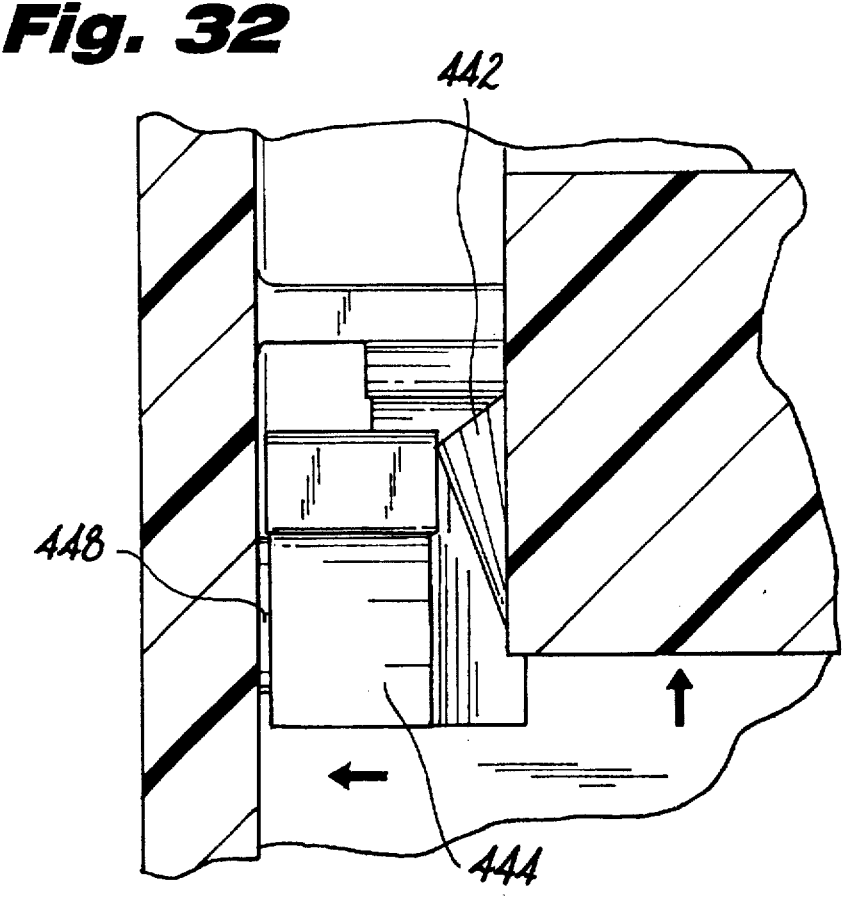
FIG. 32 illustrates a cross-sectional view of the resistor mechanism taken along section line 32—32 of FIG. 31.
Figure 33:
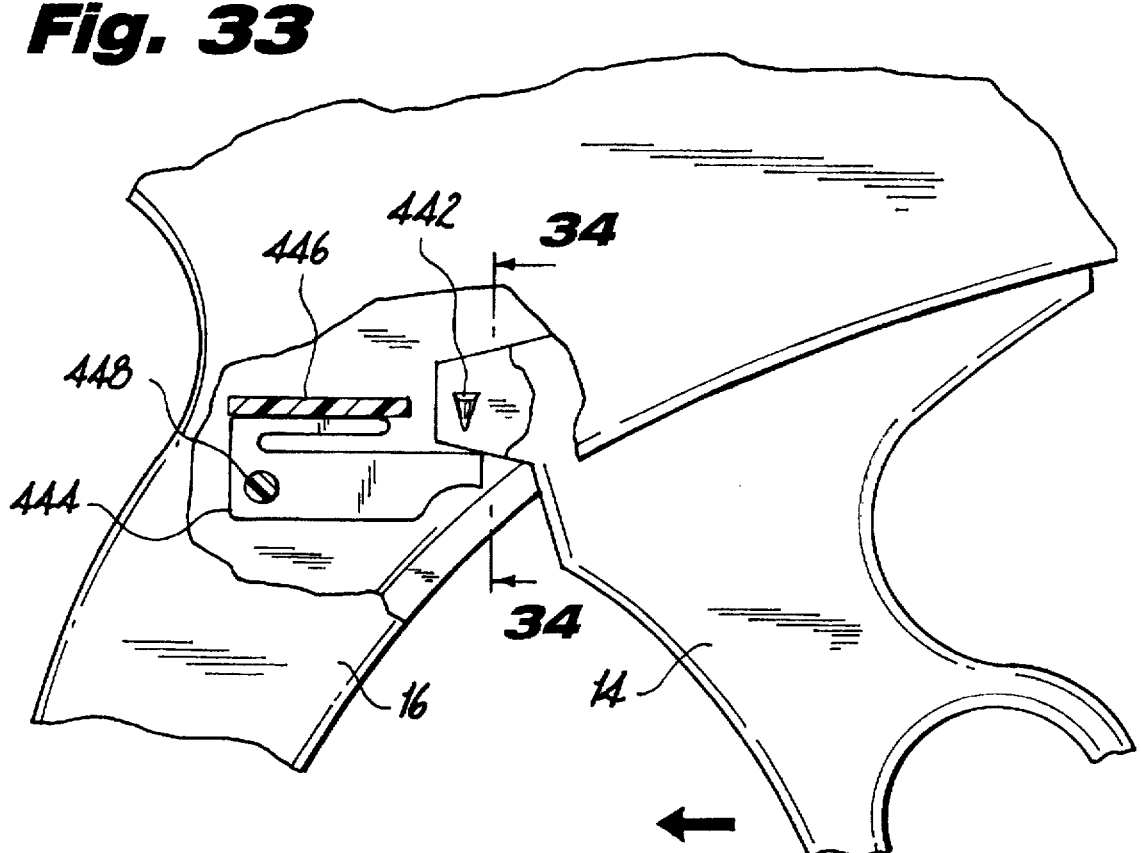
FIG. 33 illustrates a plan view in partial cut-away of the resistor mechanism of FIG. 29 upon completion of the closing stroke.
Figure 34:
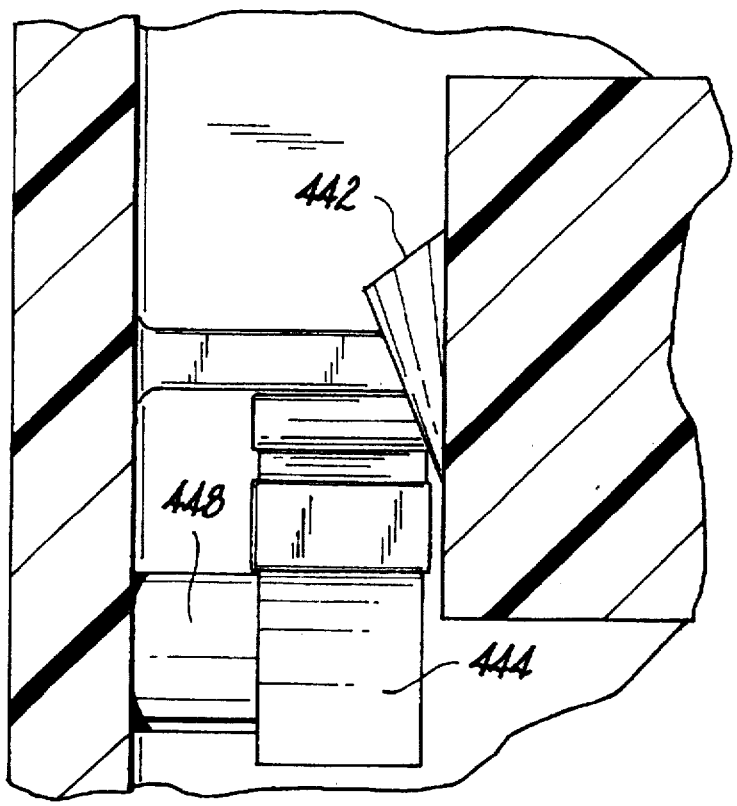
FIG. 34 illustrates a cross-sectional view taken along section line 34—34 of FIG. 33.

Referring to FIG. 29, at the initial at-rest position of the movable handle 14, the cone 442 abuts the sloped surface of the resistor 444 which is secured to the stationary hand grip 16 by a resistor pivot 448. As shown in FIG. 30, the cone 442 also has its own sloped surface contacting the resistor 444. FIG. 31 illustrates the position of the cone 442 in respect to the resistor 444 as the movable handle 14 is pulled toward the direction of the arrow. The cone 442 moves upward as the movable handle 14 pivots. As the resistor 444 is pushed upward due to the movement of the cone 442, the resistor 444 is supported by the resistor pad 446 fixed to the wall of the stationary hand grip 16 so as to provide downward resistance against the movement of the cone 442. In FIG. 32, the cone 442 also faces an additional resistance, because to move upward, the cone 442 has to push the resistor 448 outward as the lateral arrow indicates. Thus, the resistor 448 is moved toward the wall of the stationary handle 16 by the cone 442 while providing progressive resistance against upward movement of the cone 442 at the contact surfaces. In FIG. 33, the cone 442 no longer interacts with the resistor 444 as the movable handle 14 substantially completes the closure. Thus, the cone 442 no longer receives counter force from the resistor 444 while moving upward and the absence of further resistance allows a user to feel tactile indication of completion of the closure. FIG. 34 illustrates the cone 442 having a relatively flattened slope at the top portion and a steep slope at the bottom portion. The flattened sloped surface causes stronger resistance as the cone 442 moves upward and progressively contacts the surface of resistor 444. On the other hand, the steep sloped surface allows little or no resistance as the cone 442 fixed to the movable handle 14 returns to its original position. Therefore, the resistor 444 supplies heavy resistance to the cone 442 in upward movement and light resistance to the cone 442 in downward movement.

FIGS. 35-38 illustrate a slip-back preventive mechanism designed to prevent the movable handle 14 from slipping back disposed in the stationary hand grip 16 of FIG. 21. The slip-back preventive mechanism is operatively connected to the pawl member 40 connected to the movable handle 14. In FIG. 35, a slide member 450 is connected to two springs 452 so that the slide member 450 is biased toward the first teeth 100 disposed on the first rack member 48. The slide member 450 and springs 452 are disposed along the teeth 124 of the second rack member 118. The second rack member also includes a spring arm 120 which provides for flexible movement of parallel rack 118 while providing the surgeon with a different feel. The second rack member 118 further includes channels 454 therethrough on both sides thereof in parallel relationship to the teeth 124. The slide member 450, as shown in FIG. 36, includes collars 456 that can be hooked into the channel 454 of the second rack member 118. Such configuration allows the slide member 450 to slide longitudinally along the teeth 124 of the second rack member 118. FIG. 37 illustrates the pawl member 40 which is connected to the movable handle. As the movable handle is effectuated for closure, the pawl member 40 progressively contacts and moves along the teeth 100, 124 and 102 in respective order for sound and tactile indication for closure. When the pawl member 40 arrives at teeth 124 of the second rack member 118, as shown in FIG. 37 the slide member 450 comes in contact with the pawl member 40 and slides along the same direction as the arrows A indicates. This movement causes the spring members 452 to compress. When the pawl member 40 arrives at the second teeth 102 of the first rack member 48, the slide member 450 no longer engages the pawl member 40 and returns to its original position by the spring members 452 that expand from their compressed positions as shown in FIG. 38. Once pawl member 40 passes the entire length of teeth 102, it is spring biased to rotate in the direction of arrow B, thus clearing the tip of the pawl from the teeth to allow the pawl to pass back in the direction opposite to arrow A. Once it clears teeth 102, the pawl member 40 encounters frictional slip-back resistance from the slide member 450 that substantially covers the entire length of the teeth 124. To return the pawl member 40 to the original position, the movable handle 14 must be manually pulled back against the slip-back resistance operated by slide member 450 until it clears slide member 450. The pawl member 40 then passes over teeth 100 in the same manner as teeth 102 to return the handle 14 to its at rest position.

The surgical clip applying instrument of the present invention provides a number of novel features which enhance the performance of the instrument during laparoscopic or endoscopic surgical procedures.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. An apparatus for applying surgical clips comprising:
   a handle portion having a movable handle and a stationary handle;
   a body portion extending from said handle portion and including a supply of clips;
   a jaw mechanism extending from said body portion at an end opposite to said handle portion and movable between an open position for receiving a clip and a closed position for forming a clip in response to movement of said movable handle;
   a ratchet mechanism including at least one rack member and at least one pawl member disposed within said handle portion for permitting incremental closure of said jaw mechanism; and
   a slide member associated with said ratchet mechanism for preventing said movable handle from opening during a closing stroke until said closing stroke is completed, said slide member being linearly movable.

2. An apparatus according to claim 1, wherein said slide member is disposed on said ratchet mechanism for providing resistance against an opening movement of said movable handle during said closing stroke.

3. An apparatus for applying surgical clips comprising:
   a handle portion having a movable handle and a stationary handle;
   a body portion extending from said handle portion and including a supply of clips;

a jaw mechanism extending from said body portion at end opposite to said handle portion and movable between an open position for receiving a clip and a closed position for forming a clip in response to movement of said movable handle;

a ratchet mechanism including at least one rack member and at least one pawl member disposed within said handle portion for permitting incremental closure of said jaw mechanism;

a mechanism associated with said ratchet mechanism for preventing said movable handle from opening during a closing stroke until said closing stroke is completed, wherein said preventing mechanism comprises a slide member disposed on said ratchet mechanism for providing resistance against an opening movement of said movable handle during said closing stroke; and a pair of springs disposed on said ratchet mechanism for biasing said slide member against said movable handle during said closing stroke.

4. An apparatus for applying surgical clips comprising:

a handle having a movable grip and a stationary grip;

a body portion extending from the handle and including a supply of clips;

a pair of jaws extending from the body portion at an end opposite to the handle and being movable between an open position for receiving a clip and a closed position for forming a clip in response to movement of the movable grip; and at least one rack and pawl member disposed within the handle portion for permitting incremental closure of the pair of jaws, the rack and pawl member including a pair of springs and a slide member disposed on the rack and pawl member, whereby the pair of springs biases the slide member against the movable grip during the closing stroke of the movable grip, the slide member further providing resistance against an opening movement of the movable grip during the closing stroke.

* * * * *